US010716786B2

(12) United States Patent
Li et al.

(10) Patent No.: US 10,716,786 B2
(45) Date of Patent: Jul. 21, 2020

(54) TRANSMUCOSAL AND SUBCUTANEOUS COMPOSITIONS

(71) Applicant: INTRA-CELLULAR THERAPIES, INC., New York, NY (US)

(72) Inventors: Peng Li, New Milford, NJ (US); Wei Yao, New Milford, NJ (US); Robert Davis, San Diego, CA (US)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 301 days.

(21) Appl. No.: 15/934,860

(22) Filed: Mar. 23, 2018

(65) Prior Publication Data

US 2018/0271862 A1 Sep. 27, 2018

Related U.S. Application Data

(60) Provisional application No. 62/476,538, filed on Mar. 24, 2017.

(51) Int. Cl.
| A61K 31/498 | (2006.01) |
| A61K 31/4985 | (2006.01) |
| A61K 9/06 | (2006.01) |
| A61K 9/00 | (2006.01) |

(52) U.S. Cl.
CPC .......... *A61K 31/4985* (2013.01); *A61K 9/006* (2013.01); *A61K 9/0036* (2013.01); *A61K 9/0043* (2013.01); *A61K 9/06* (2013.01)

(58) Field of Classification Search
CPC .................................................... A61K 31/498
USPC ........................................................ 514/250
See application file for complete search history.

(56) References Cited

U.S. PATENT DOCUMENTS

| 2,490,813 | A | 12/1949 | Hughes et al. |
| 3,299,078 | A | 1/1967 | Pachter |
| 3,813,392 | A | 5/1974 | Sellstedt et al. |
| 3,914,421 | A | 10/1975 | Rajagopalan |
| 4,001,263 | A | 1/1977 | Plattner et al. |
| 4,115,577 | A | 9/1978 | Rajagopalan |
| 4,136,145 | A | 1/1979 | Fuchs et al. |
| 4,183,936 | A | 1/1980 | Rajagopalan |
| 4,219,550 | A | 8/1980 | Rajagopalan |
| 4,238,607 | A | 12/1980 | Rajagopalan |
| 4,389,330 | A | 6/1983 | Tice et al. |
| 4,522,944 | A | 6/1985 | Doria et al. |
| 4,530,840 | A | 7/1985 | Tice et al. |
| 4,849,246 | A | 7/1989 | Schmidt |
| 4,971,971 | A | 11/1990 | Tokunaga et al. |
| 4,985,432 | A | 1/1991 | Tokunaga et al. |
| 5,114,976 | A | 5/1992 | Norden |
| 5,151,419 | A | 9/1992 | Perenyi et al. |
| 5,538,739 | A | 7/1996 | Bodmer et al. |
| 5,576,460 | A | 11/1996 | Buchwald et al. |
| 5,629,003 | A | 5/1997 | Horstmann et al. |
| 5,648,539 | A | 7/1997 | Goodbrand |
| 5,648,542 | A | 7/1997 | Goodbrand et al. |
| 5,654,482 | A | 8/1997 | Goodbrand |
| 5,705,697 | A | 1/1998 | Goodbrand et al. |
| 5,723,669 | A | 3/1998 | Goodbrand et al. |
| 5,723,671 | A | 3/1998 | Goodbrand et al. |
| 5,763,476 | A | 6/1998 | Delbressine et al. |
| 5,847,166 | A | 12/1998 | Buchwald et al. |
| 5,902,901 | A | 5/1999 | Goodbrand et al. |
| 5,948,430 | A | 9/1999 | Zerbe et al. |
| 6,043,370 | A | 3/2000 | Kubo et al. |
| 6,166,226 | A | 12/2000 | Buchwald et al. |
| 6,221,335 | B1 | 4/2001 | Foster |
| 6,235,936 | B1 | 5/2001 | Buchwald et al. |
| 6,307,087 | B1 | 10/2001 | Buchwald et al. |
| 6,323,366 | B1 | 11/2001 | Wolfe et al. |
| 6,395,916 | B1 | 5/2002 | Buchwald et al. |
| 6,407,092 | B1 | 6/2002 | Hester et al. |
| 6,440,710 | B1 | 8/2002 | Keinan et al. |
| 6,465,693 | B2 | 10/2002 | Buchwald et al. |
| 6,541,639 | B2 | 4/2003 | Zhou et al. |
| 6,544,559 | B2 | 4/2003 | Mesens et al. |
| 6,548,493 | B1 | 4/2003 | Robichaud et al. |
| 6,552,017 | B1 | 4/2003 | Robichaud et al. |
| 6,552,024 | B1 | 4/2003 | Chen et al. |
| 6,603,008 | B1 | 8/2003 | Ando et al. |
| 6,699,852 | B2 | 3/2004 | Robichaud et al. |
| 6,713,471 | B1 | 3/2004 | Robichaud et al. |
| 6,759,554 | B2 | 7/2004 | Buchwald et al. |

(Continued)

FOREIGN PATENT DOCUMENTS

| EP | 0 058 481 | 8/1982 |
| EP | 0 856 508 | 8/1998 |

(Continued)

OTHER PUBLICATIONS

Alvir, et al., "Clozapine-Induced Agranulocytosis," *The New England Journal of Medicine*, vol. 329, No. 3, pp. 162-167, (1993).
Avendano, et al., "The problem of the existence of C(Ar)-H . . . N Intramolecular Hydrogen Bonds in a Family of 9-Azaphenyl-9H-carbazoles," *J. Chem. Soc. Perkin Trans.*, vol. 2, pp. 1547-1555, (1993).
Baille, T.A., "The Use of Stable Isotopes in Pharmacological Research," *Pharmacol. Reviews*, vol. 33, No. 2, pp. 81-132, (1981).
Balbach, et al., "Pharmaceutical evaluation of early development candidates 'the 100 mg-approach'," *International Journal of Pharmaceutics*, vol. 275, pp. 1-12, (2004).
Bastin, et al.,"Salt Selection and Optimisation Procedures for Pharmaceutical New Chemical Entities," *Organic Process and Research Development*, vol. 4, No. 5, pp. 427-435 (2000).

(Continued)

*Primary Examiner* — Raymond J Henley, III
(74) *Attorney, Agent, or Firm* — Hoxie & Associates LLC

(57) ABSTRACT

The disclosure provides new transmucosal and subcutaneous pharmaceutical compositions comprising 1-(4-fluoro-phenyl)-4-((6bR,10aS)-3-methyl-2,3,6b,9,10,10a-hexahydro-1H,7H-pyrrolo[3',4':4,5]pyrrolo[1,2,3-de]quinoxalin-8-yl)-butan-1-one or 1-(4-fluoro-phenyl)-4-((6bR,10aS)-2,2-d$_2$-3-methyl-2,3,6b,9,10,10a-hexahydro-1H,7H-pyrido[3',4':4,5]pyrrolo[1,2,3-de]quinoxalin-8-yl)-butan-1-one or comprising -(4-fluoro-phenyl)-4-((6bR,10aS)-1,1,2,2-d$_4$-3-methyl-2,3,6b,9,10,10a-hexahydro-1H,7H-pyrido[3',4':4,5] pyrrolo[1,2,3-de]quinoxalin-8-yl)-butan-1-one, in free base, co-crystal or salt form, together with methods of making and using them.

24 Claims, No Drawings

(56) References Cited

U.S. PATENT DOCUMENTS

| | | |
|---|---|---|
| 6,762,329 B2 | 7/2004 | Marcoux et al. |
| 6,828,314 B2 | 12/2004 | Frank et al. |
| 6,849,619 B2 | 2/2005 | Robichaud et al. |
| 6,849,640 B2 | 2/2005 | Ennis et al. |
| 6,867,298 B2 | 3/2005 | Buchwald et al. |
| 6,888,032 B2 | 5/2005 | Buchwald et al. |
| 6,946,560 B2 | 9/2005 | Buchwald et al. |
| 7,026,498 B2 | 4/2006 | Buchwald et al. |
| 7,071,186 B2 | 7/2006 | Robichaud et al. |
| 7,109,339 B2 | 9/2006 | Lee et al. |
| 7,115,784 B2 | 10/2006 | Buchwald et al. |
| 7,183,282 B2 | 2/2007 | Robichaud et al. |
| 7,223,879 B2 | 5/2007 | Buchwald et al. |
| RE39,679 E | 6/2007 | Robichaud et al. |
| RE39,680 E | 6/2007 | Robichaud et al. |
| 7,238,690 B2 | 7/2007 | Robichaud et al. |
| 7,247,731 B2 | 7/2007 | Buchwald et al. |
| 7,323,608 B2 | 1/2008 | Buchwald et al. |
| 7,375,226 B2 | 5/2008 | Jolidon et al. |
| 7,462,641 B2 | 12/2008 | Igo et al. |
| 7,517,990 B2 | 4/2009 | Ito et al. |
| 7,592,454 B2 | 9/2009 | Lee et al. |
| 7,614,727 B2 | 11/2009 | Hori |
| 7,645,752 B2 | 1/2010 | McDevitt et al. |
| 7,998,971 B2 | 8/2011 | Barlow et al. |
| 8,309,772 B2 | 11/2012 | Weiner et al. |
| 8,414,922 B2 | 4/2013 | Bryson et al. |
| 8,461,148 B2 | 6/2013 | Hollander |
| 8,603,514 B2 | 12/2013 | Yang et al. |
| 8,652,378 B1 | 2/2014 | Yang et al. |
| 8,697,700 B2 | 4/2014 | Surman et al. |
| 8,779,139 B2 | 7/2014 | Tomesch et al. |
| 8,791,138 B2 | 7/2014 | Seeman et al. |
| 8,835,459 B2 | 9/2014 | Kottayil et al. |
| 8,900,497 B2 | 12/2014 | Yang et al. |
| 8,900,498 B2 | 12/2014 | Yang et al. |
| 8,906,277 B2 | 12/2014 | Yang et al. |
| 9,108,340 B2 | 8/2015 | Yang et al. |
| 9,168,258 B2 | 10/2015 | Mates et al. |
| 9,199,995 B2 | 12/2015 | Tomesch et al. |
| 9,216,175 B2 | 12/2015 | Amancha et al. |
| 9,315,504 B2 | 4/2016 | Tomesch et al. |
| 9,371,324 B2 | 6/2016 | Mates et al. |
| 9,393,192 B2 | 7/2016 | Yam et al. |
| 9,427,412 B2 | 8/2016 | Bryson et al. |
| 9,567,327 B2 | 2/2017 | Xiong et al. |
| 9,586,960 B2 | 3/2017 | Tomesch et al. |
| 9,616,061 B2 | 4/2017 | Mates et al. |
| 9,708,322 B2 | 7/2017 | Li et al. |
| 9,745,300 B2 | 8/2017 | Mates et al. |
| 9,751,883 B2 | 9/2017 | Tomesch et al. |
| 9,956,227 B2 | 5/2018 | Vanover et al. |
| 10,072,010 B2 | 9/2018 | Li et al. |
| 10,077,267 B2 | 9/2018 | Mates et al. |
| 10,117,867 B2 | 11/2018 | Mates et al. |
| 2001/0008942 A1 | 7/2001 | Buchwald et al. |
| 2004/0034015 A1 | 2/2004 | Robichaud et al. |
| 2004/0092534 A1 | 5/2004 | Yam et al. |
| 2004/0127482 A1 | 7/2004 | Robichaud et al. |
| 2004/0142970 A1 | 7/2004 | Chung et al. |
| 2004/0180875 A1 | 9/2004 | Lee et al. |
| 2004/0186136 A1 | 9/2004 | Alken et al. |
| 2004/0209864 A1 | 10/2004 | Robichaud et al. |
| 2005/0166771 A1 | 8/2005 | Gygi et al. |
| 2005/0222209 A1 | 10/2005 | Zeldis et al. |
| 2005/0222238 A1 | 10/2005 | Alken |
| 2006/0178362 A1 | 8/2006 | Robichaud et al. |
| 2006/0205787 A1 | 9/2006 | Muller et al. |
| 2007/0082929 A1 | 4/2007 | Gant et al. |
| 2007/0197695 A1 | 8/2007 | Potyen et al. |
| 2008/0069885 A1 | 3/2008 | Mesens et al. |
| 2008/0132552 A1 | 6/2008 | Kleinman et al. |
| 2008/0280941 A1 | 11/2008 | Lourtie |
| 2009/0076159 A1 | 3/2009 | Czarnik |
| 2009/0209608 A1 | 8/2009 | Czarnik |
| 2010/0113781 A1 | 5/2010 | Tomesch et al. |
| 2010/0159033 A1 | 6/2010 | Gant et al. |
| 2011/0071080 A1 | 3/2011 | Mates et al. |
| 2011/0112105 A1 | 5/2011 | Tomesch et al. |
| 2012/0196814 A1 | 8/2012 | Gong et al. |
| 2013/0202692 A1 | 8/2013 | Mates et al. |
| 2014/0210117 A1 | 7/2014 | Friesen et al. |
| 2015/0004237 A1 | 1/2015 | Edgar et al. |
| 2015/0031804 A1 | 1/2015 | Shiramizu et al. |
| 2015/0072964 A1 | 3/2015 | Mates et al. |
| 2015/0079172 A1 | 3/2015 | Mates et al. |
| 2015/0080404 A1 | 3/2015 | Mates et al. |
| 2016/0235720 A1 | 8/2016 | Foster et al. |
| 2016/0354315 A1 | 12/2016 | Li |
| 2017/0114037 A1 | 4/2017 | Davis et al. |
| 2017/0183350 A1 | 6/2017 | Mates et al. |
| 2017/0189398 A1 | 7/2017 | Mates et al. |
| 2017/0283417 A1 | 10/2017 | Li et al. |
| 2017/0319580 A1 | 11/2017 | Yao et al. |
| 2018/0044337 A1 | 2/2018 | Tomesch et al. |
| 2018/0200256 A1 | 7/2018 | Vanover et al. |
| 2019/0071445 A1 | 3/2019 | Li et al. |
| 2019/0183888 A1 | 6/2019 | Mates et al. |
| 2019/0231780 A1 | 8/2019 | Yao et al. |

FOREIGN PATENT DOCUMENTS

| | | |
|---|---|---|
| EP | 0 976 732 | 2/2000 |
| EP | 1 245 553 | 10/2002 |
| EP | 1 254 884 | 11/2002 |
| EP | 1 539 115 | 6/2005 |
| EP | 1 564 671 | 8/2005 |
| GB | 1476087 | 6/1977 |
| GB | 2145422 | 3/1985 |
| RU | 2465267 | 10/2012 |
| WO | WO 1994/024125 | 10/1994 |
| WO | WO 1995/013814 | 5/1995 |
| WO | WO 1995/026325 | 10/1995 |
| WO | WO 1998/015515 | 4/1998 |
| WO | WO 1998/043956 | 10/1998 |
| WO | WO 1999/043643 | 9/1999 |
| WO | WO 2000/002887 | 1/2000 |
| WO | WO 2000/035419 | 6/2000 |
| WO | WO 2000/048610 | 8/2000 |
| WO | WO 2000/064899 | 11/2000 |
| WO | WO 2000/077001 | 12/2000 |
| WO | WO 2000/077002 | 12/2000 |
| WO | WO 2000/077010 | 12/2000 |
| WO | WO 2002/059129 | 8/2002 |
| WO | WO 2002/085838 | 10/2002 |
| WO | WO 2003/014118 | 2/2003 |
| WO | WO 2004/010981 | 2/2004 |
| WO | WO 2004/013094 | 2/2004 |
| WO | WO 2004/039788 | 5/2004 |
| WO | WO 2004/045668 | 6/2004 |
| WO | WO 2004/056324 | 7/2004 |
| WO | WO 2005/030214 | 4/2005 |
| WO | WO 2006/034187 | 3/2006 |
| WO | WO 2006/081251 | 8/2006 |
| WO | WO 2006/081332 | 8/2006 |
| WO | WO 2007/025103 | 3/2007 |
| WO | WO 2007/084841 | 7/2007 |
| WO | WO 2008/112280 | 9/2008 |
| WO | WO 2009/017836 | 2/2009 |
| WO | WO 2009/100324 | 8/2009 |
| WO | WO 2009/114181 | 9/2009 |
| WO | WO 2009/145900 | 12/2009 |
| WO | WO 2011/133224 | 10/2011 |
| WO | WO 2013/155504 | 10/2013 |
| WO | WO 2013/155505 | 10/2013 |
| WO | WO 2013/155506 | 10/2013 |
| WO | WO 2014/110322 | 7/2014 |
| WO | WO 2014/145192 | 9/2014 |
| WO | WO 2015/085004 | 6/2015 |
| WO | WO 2015/154025 | 10/2015 |
| WO | WO 2015/154030 | 10/2015 |
| WO | WO 2015/191554 | 12/2015 |
| WO | WO 2017/117514 | 7/2017 |
| WO | WO 2017/132408 | 8/2017 |

(56) References Cited

FOREIGN PATENT DOCUMENTS

| | | |
|---|---|---|
| WO | WO 2017/165843 | 9/2017 |
| WO | WO 2017/172784 | 10/2017 |
| WO | WO 2018/031535 | 2/2018 |
| WO | WO 2018/106916 | 6/2018 |
| WO | WO 2018/175969 | 9/2018 |
| WO | WO 2018/189646 | 10/2018 |
| WO | WO 2019/102240 | 5/2019 |

OTHER PUBLICATIONS

Beletskaya, et al., "Pd- and Cu-catalyzed selective arylation of benzotriazole," *Tetrahedron Letters*, vol. 39, pp. 5617-5620, (1998).
Bennett, et al., "Cecil Textbook of Medicine," 20th Edition, vol. 1, pp. 1004-1010, (1996).
Berger, et al., "Synthesis of Some Conformationally Restricted Analogs of Fentanyl," *Journal of Medicinal Chemistry*, vol. 20, No. 4, pp. 600-602, (1977).
Boger, et al., "Inverse Electron Demand Diels-Alder Reactions of Heterocyclic Aza Dienes. Studies on the Total Synthesis of Lavendamycin: Investigative Studies on the Preparation of the CDE β-Carboline Ring System and AB Quinoline-5,8-quinone Ring System," *J. Org. Chem.*, vol. 50, pp. 5782-5789, (1985).
Bowman, et al., "Intramolecular Aromatic Substitution ($S_{RN}1$) Reactions—Use of Entrainment for the Preparation of Benzothiazoles," *Tetrahedron Letters*, vol. 23, pp. 5093-5096, (1982).
Bowman, et al., "Copper (1) Catalysed Aromatic Nucleophilic Substitution: A Mechanistic and Synthetic Comparison with the $S_{RN}1$ Reaction," *Tetrahedron Letters*, vol. 25, No. 50, pp. 5821-5824, (1984).
Bowman, et al., "Synthesis of 1H-quinazoline-4-ones Using Intramolecular Aromatic Nucelophilic Substitution," *ARKIVOC*, vol. x, pp. 434-442 (2003).
Bremner, et al., "Neuroimaging of Posttraumatic Stress Disorder", *Psychiatric Annals Journal*, vol. 28, No. 8, p. 445-450, (1998).
Browne, T.R., "Stable Isotope Techniques in Early Drug Development: An Economic Evaluation," *J. Clin. Pharmacol.*, vol. 38, pp. 213-220, (1998).
Bryan-Lluka, et al., "Potencies of Haloperidol Metabolites as Inhibitors of the Human Noradrenaline, Dopamine and Serotonin Transporters in Transfected COS-7 Cells," *Naunyn-Shemiedeberg's Arch Pharmacol*, vol. 360, pp. 109-115, (1999).
Byrn, et al., "Pharmaceutical Solids: A Strategic Approach to Regulatory Considerations," *Pharmaceutical Research*, vol. 12, No. 7, pp. 945-954, (1995).
Caira, M.R., "Crystalline Polymorphism of Organic Compounds," *Topics in Current Chemistry*, vol. 198, p. 163-203, (1998).
Cherrah, et al., "Study of Deuterium Isotope Effects on Protein Binding by Gas Chromatography/Mass Spectrometry. Caffeine and Deuterated Isotopomers," *Biomedical and Environmental Mass Spectrometry*, vol. 14, pp. 653-657, (1987).
Crawford, et al., "Copper-Catalyzed Amidations of Bromo Substituted Furans and Thiophenes," *Tetrahedron Letters*, vol. 43, pp. 7365-7368, (2002).
Darmani, et al., "Do Functional Relationships Exist Between 5-$HT_{1A}$ and 5-$HT_2$ Receptors?" *Pharmacology and Biochemistry & Behavior*, vol. 36, pp. 901-906, (1990).
Davis, et al., "ITI-007 demonstrates brain occupancy at serotonin 5-$HT_{2A}$ and dopamine $D_2$ receptors and serotonin transporters using positron emission tomography in healthy volunteers," *Psychopharmacology*, vol. 232, pp. 2863-2872, (2015); DOI: 10.1007/s00213-015-3922-1.
Davis, et al., "ITI-007 in the Treatment of Schizophrenia: From Novel Pharmacology to Clinical Outcomes," *Expert Review of Neurotherapeutics*, vol. 16, No. 6, pp. 601-614, (2016).
Dyck, et al., "Effects of Deuterium Substitution on the Catabolism of β-Phenylethylamine. An In Vivo Study," *Journal of Neurochemistry*, vol. 46, Issue 2, pp. 399-404, (1986).

Evindar, et al., "Copper- and Palladium-Catalyzed Intramolecular Aryl Guanidinylation: An Efficient Method for the Synthesis of 2-Aminobenzimidazoles", *Organic Letters*, vol. 5, No. 2, pp. 133-136, (2003).
Ezquerra, et al., "Efficient Reagents for the Synthesis of 5-, 7-, and 5, 7-Substitued Indoles Starting from Aromatic Amines: Scope and Limitations", *J. Org. Chem.*, vol. 61, pp. 5804-5812, (1996).
Fawcett, J., "Posttraumatic Stress Disorder, Stress, and Happiness", *Psychiatric Annals Journal*, vol. 28, No. 8, pp. 427-428, (1998).
Fee, et al., "Copper (II)-Promoted Solvolyses of Nickel (II) Complexes III. Tetradentate Schiff Base Ligands Containing Various Diamine Segments," *Aust. J. Chem.*, vol. 26, pp. 1475-1485, (1973).
Ferreira, et al., "Novel Synthetic Routes to Thienocarbazoles Via Palladium or Copper Catalyzed Amination or Amidation of Arylhalides and Intramolecular Cyclization", *Tetrahedron*, vol. 58, pp. 7943-7949, (2002).
Finet, et al., "Recent Advances in Ullmann Reaction: Copper (II) Diacetate Catalysed N-, )-and S-arylation Involving Polycoordinate Heteroatomic Derivatives," *Current Organic Chemistry*, vol. 6, pp. 597-626, (2002).
Foster, A.B., "Deuterium Isotope Effects in the Metabolism of Drugs and Xenobiotics: Implications for Drug Design," *Advances in Drug Research*, vol. 14, pp. 1-40, (1985).
Foster, et al., "Acetylcholinesterase Inhibitors Reduce Spreading Activation in Dementia," *Neuropsychologia*, vol. 50, pp. 2093-2099, (2012).
Friedman, M.J.., "Current and Future Drug Treatment for Post-traumatic Stress Disorder Patients", *Psychiatric Annals Journal*, vol. 28, No. 8, pp. 464-468, (1998).
Goodbrand, et al., "Ligand-Accelerated Catalysis of the Ullmann Condensation: Application to Hole Conducting Triarylamines," *J. Org. Chem.*, vol. 64, pp. 670-674, (1999).
Gouyette, A., "Synthesis of Deuterium-labelled Elliptinium and its Use in Metabolic Studies," *Biomedical and Environmental Mass Spectrometry*, vol. 15, pp. 243-247, (1988).
Grant, D., "Theory and Origin and Polymorphism", *Polymorphism in Pharmaceutical Solids*, Chapter 1, pp. 1-10, (1999).
Guillory, J.K., "Generation of Polymorphs, Hydrates, Solvates, and Amorphous Solids", *Polymorphism in Pharmaceutical Solids*, Chapter 5, pp. 183-226, (1999).
Hackam, et al., "Translation of Research Evidence from Animals to Humans," *JAMA*, vol. 296, No. 14, pp. 1731-1732, (2006).
Hamann, et al., "Systematic Variation of Bidentate Ligands Used in Aryl Halide Amination. Unexpected Effects of Steric, Electronic, and Geometric Perturbations", *J. Am. Chem. Soc.*, vol. 120, pp. 3694-3703, (1998).
Harbert, et al., "Neuroleptic Activity in 5-Aryltetrahydro-γ-carbolines", *J. Med. Chem.*, vol. 23, pp. 635-643, (1980).
Hartwig, J., "Palladium-Catalyzed Amination of Aryl Halides: Mechanism and Rational Catalyst Design," *Synlett*, pp. 329-340, (1996).
Harvey, et al., "Serotonin and Stress: Protective or Malevolent Actions in the Biobehavioral Response to Repeated Trauma?," *Annals of the New York Academy of Sciences*, vol. 1032, pp. 267-272, (2004); DOI: 10.1196/annals.1314.035.
Haskins, N.J., "The Application of Stable Isotopes in Biomedical Research," *Biological Mass Spectrometry*, vol. 9, No. 7, pp. 269-277, (1982).
Hassan, et al., "Aryl-aryl Bond Formation One Century After the Discovery of the Ullmann Reaction," *Chem. Rev.*, vol. 102, pp. 1359-1469, (2002).
Haynes, et al., "Occurrence of Pharmaceutically Acceptable Anions and Cations in the Cambridge Structural Database", *Journal of Pharmaceutical Sciences*, vol. 94, No. 10, pp. 2111-2120, (2005).
Honma, S., et al., "The Metabolism of Roxatidine Acetate Hydrochloride: Liberation of Deuterium from the Piperidine Ring during Hydroxylation," *Drug Metabolism and Disposition*, vol. 15, No. 4, pp. 551, (1987).
International Preliminary Report on Patentability for International Application No. PCT/US2013/036514 dated Oct. 14, 2014.
International Search Report issued in International Application No. PCT/US2008/003340, dated Aug. 8, 2008, 3 pages.

(56) References Cited

OTHER PUBLICATIONS

International Search Report issued in International Application No. PCT/US2009/001608, dated Apr. 27, 2009, 3 pages.
International Search Report issued in International Application No. PCT/US2009/003261, dated Jul. 16, 2009.
International Search Report issued in International Application No. PCT/US2011/00719, dated Jul. 5, 2011, 3 pages.
International Search Report issued in International Application No. PCT/US2013/036515, dated Aug. 13, 2013, 3 pages.
International Search Report issued in International Application No. PCT/US2013/036514, dated Aug. 16, 2013, 3 pages.
International Search Report issued in International Application No. PCT/US2013/036512, dated Aug. 19, 2013, 4 pages.
International Search Report issued in International Application No. PCT/US2015/024340, dated Jun. 25, 2015, 2 pages.
International Search Report issued in International Application No. PCT/US2015/024345, dated Jun. 25, 2015, 3 pages.
Ito, et al., "Studies of Organic Catalytic Reactions. VI. The Function of Pyridine and Copper in the Rosenmund-von Braun Reaction," *Bulletin of the Chemical Society of Japan*, vol. 41, pp. 419-423, (1968).
Izrayelit, L., "Schizoaffective Disorder and PTSD Successfully Treated With Olanzapine and Supportive Psychotherapy", *Psychiatric Annals Journal*, vol. 28, No. 8, pp. 424-426, (1998).
Jain et al., "Polymorphism in Pharmacy," *Indian Drugs*, vol. 23, No. 6, pp. 315-316, (1986).
Ji, et al., "Selective Amination of Polyhalopyridines Catalyzed by a Palladium-xantphos Complex," *Organic Letters*, vol. 5, No. 24, pp. 4611-4614, (2003).
Jordan, V.C., "Tamoxifen: A Most Unlikely Pioneering Medicine," *Nature Reviews: Drug Discovery*, vol. 2, pp. 205-213, (2003).
Juorio, A.V., et al., "Effects of Acute and Chronic Phenelzine on Regional Monoamine Metabolism in Rats and its Potentiation by Deuterium Substitution," *Naunyn-Schmiedeberg's Archives of Pharmacology*, vol. 333, No. 3, pp. 240-245, (1986); Abstract only.
Kametani, et al., "A Novel Synthesis of Indole Derivatives," *Heterocycles*, vol. 14 No. 3, pp. 277-280, (1980).
Kang, et al., "Copper-catalyzed N-arylation of Aryl Iodides with Benzamides or Nitrogen Heterocycles in the Presence of Ethylendiamine," *Synlett*, No. 3, pp. 427-430, (2002).
Kay, et al., "The Positive and Negative Syndrome Scale (PANSS) for Schizophrenia," *Schizophrenia Bulletin*, vol. 13, No. 2, pp. 261-276, (1987).
Kessler, et al., "Lifetime Prevalence and Age-of-Onset Distributions of DSM-IV Disorders in the National Comorbidity Survey Replication," *Arch Gen Psychiatry*, vol. 62, pp. 593-602, (2005).
Khorana, et al., "Gamma-Carbolines: Binding at 5-HT5A Serotonin Receptors," *Bioorganic & Medicinal Chemistry*, vol. 11, pp. 717-722, p. 718 Table 1, (2003).
Kiyomori, et al., "An Efficient Copper-catalyzed Coupling of Aryl Halides with Imidazoles," *Tetrahedron Letters*, vol. 40, pp. 2657-2660, (1999).
Klapars, et al., "A General and Efficient Copper Catalyst for the Amidation of Aryl Halides and the N-arylation of Nitrogen Heterocycles," *J. Am. Chem. Soc.*, vol. 123, pp. 7727-7729, (2001).
Klapars, et al., "A General and Efficient Copper Catalyst for the Amidation of Aryl Halides," *J. Am. Chem. Soc.*, vol. 124, pp. 7421-7428, (2002).
Kondratov, et al., "Nucelophilic Substitution in the Aromatic Series. Lv. Reaction of o-nitrochlorobenzene with Ammonia in the Presence of Copper Compounds," *Zhurnal Organidreskoi Khimii*, vol. 51, No. 11, pp. 2387-2390, (1979).
Koppel, et al., "Optimal Treatment of Alzheimer's Disease Psychosis: Challenges and Solutions," *Neuropsychiatric Disease and Treatment*, vol. 10, pp. 2253-2262, (2014).
Kwong, et al., "Mild and Efficient Copper-catalyzed Amination of Aryl Bromides with Primary Alkylamines," *Organic Letters*, vol. 5, No. 6, pp. 793-796, (2003).
Lebert, et al., "Trazodone in Fronto-Temporal Dementia," *Research and Practice in Alzheimer's Disease*, vol. 11, pp. 356-360, (2006).

Lee, et al. "Novel, Highly Potent, Selective 5-$HT_{2A}$/$D_2$ Receptor Antagonists as Potential Atypical Antipsychotics," *Bioorg. Med. Chem. Lett.*, vol. 13, pp. 767-770, (2003).
Li, et al., "Discovery of a Tetracyclic Quinoxaline Derivative as a Potent and Orally Active Multifunctional Drug Candidate for the Treatment of Neuropsychiatric and Neurological Disorders," *Journal of Medicinal Chemistry*, vol. 57, pp. 2670-2682, (2014).
Lieberman, et al., "ITI-007 for the Treatment of Schizophrenia: A 4-Week Randomized, Double-Blind, Controlled Trial," *Biol. Psychiatry*, vol. 79, No. 12, pp. 952-961, (2015).
Lin, et al., "Dosage and Duration of Antipsychotic Treatment in Demented Outpatients with Agitation or Psychosis," *Journal of the Formosan Medical Association*, vol. 114, pp. 147-153, (2015).
Lipschitz, et al., "Childhood Posttraumatic Stress Disorder: A Review of Neurobiologic Sequelae," *Psychiatric Annals Journal*, vol. 28, No. 8, pp. 452-457, (1998).
Lopez, et al., "Psychiatric Symptoms Vary with the Severity of Dementia in Probably Alzheimer's Disease," *J. Neuropsychiatry Clin. Neurosc.*, vol. 15, No. 3, pp. 346-353, (2003).
Louie, et al., "Palladium-Catalyzed Synthesis of Arylamines from Aryl Halides, Mechanistic Studies lead to Coupling in the Absence of Tin Reagents," *Tetrahedron Letters*, vol. 36, No. 21, pp. 3609-3612, (1995).
Lounkine, et al., "Formal Concept Analysis for the Identification of Molecular Fragment Combinations Specific for Active and Highly Potent Compounds," *J. Med. Chem.*, vol. 51, No. 17, pp. 5342-5348, (2008).
Madhusoodanan, et al., "Pharmacological Management of Behavioral Symptoms Associated with Dementia," *World J. Psychiatr.*, vol. 4, No. 4, pp. 72-79, (2014).
March, et al, *Advanced Organic Chemistry; Reactions, Mechanisms and Structures*, Fourth Edition, pp. 910-911, (1992).
Marcoux, et al., "A General Copper-catalyzed Synthesis of Diaryl Ethers," *J. Am. Chem. Soc.*, vol. 119, pp. 10539-10540, (1997).
Mohamed, et al., "Pharmacotherapy of PTSD in the U.S. Department of Veterans Affairs: Diagnostic- and Symptom-guided Drug Selection," *J. Clin. Psychiatry*, vol. 69, pp. 959-965, (2008).
Morgan, et al., "Acoustic Startle in Individuals With Posttraumatic Stress Disorder," *Psychiatric Annals Journal*, vol. 28, Issue 8, pp. 430-434, (1998).
Mulrooney, et al., "Recent Developments in Copper-catalyzed N-Arylation with Aryl Halides," *Essay—University of Pennsylvania*, (2004).
Murakami, et al., "Fischer Indolization of Ethyl Pyruvate 2-[2-(Trifluoromethyl)phenyl]-phenylhydrazone and New Insight into the Mechanism of the Goldberg Reaction," *Chem. Pharm. Bull*, vol. 43, No. 8, pp. 1281-1286, (1995).
Nagai, et al., "Synthesis of 2,3,4,4a,5,9b-hexahydro-1H-pyrido[4,3-b] indole Derivatives and Their Central Nervous System Activities," *Journal of Medicinal Chemistry*, vol. 22, No. 6, pp. 677-683, (1979).
Newman, et al., "Solid-state Analysis of the Active Pharmaceutical Ingredient in Drug Products," *Drug Discovery Today*, vol. 8, No. 19, pp. 898-903, (2003).
Nihon rounen igaku zasshi, vol. 48, No. 3, pp. 195-204, (2011 nen). Partial English translation only, 2 pages.
Pieniaszek, et al., "Moricizine Bioavailability via Simultaneous Dual, Stable Isotope Administration: Bioequivalence Implications," *J. Clin. Pharmacol.*, vol. 39, pp. 817-825, (1999).
Pond, et al., "Stereospecific Reduction of Haloperidol in Human Tissues," *Biochemical Pharmacology*, vol. 44, No. 5, pp. 867-871, (1992).
"Protection for the Amino Group," *Protective Groups in Organic Synthesis*, Third Edition, John Wiley & Sons, Inc., pp. 494-505, (1999).
PubChem, OPEN Chemistry Database, Compound Summary for CID-22036753, pp. 4, (2007), 12 pages.
Rackova, et al., "Free Radical Scavenging and Antioxidant Activities of Substituted Hexahydropyridoindoles. Quantitative Structure-Activity Relationships." *Journal of Medicinal Chemistry*, vol. 49, No. 8, pp. 2543-2548, (2006).
Rainer, M.K., "Risperidone Long-acting Injection: A Review of its Long Term Safety and Efficacy," *Neuropsychiatric Disease and Treatment*, vol. 4, No. 5, pp. 919-927, (2008).

(56) References Cited

OTHER PUBLICATIONS

Rye (Sleep Disorders and Parkinson's Disease, 2000, accessed online http://www.waparkinsons.org/edu_research/articles/Sleep_Disorders.html), 2 pages.
Sadighi, et al., "A Highly Active Palladium Catalyst System for the Arylation of Anilines," *Tetrahedron Letters*, vol. 39, pp. 5327-5330, (1998).
Savjani, et al., "Drug Solubility: Importance and Enhancement Techniques," *International Scholarly Research Network Pharmaceutics*, vol. 2012, pp. 1-10, (2012).
"Securities," Bennett v. Alkermes, Inc., at http://securities.stanford.edu/filings-documents/1029/ALKS03-01/20031029_r01c_0312091.pdf (retrieved from the internet on Jun. 13, 2017), (2003).
Sigel, et al., "Tenary Complexes in Solution," *Inorganic Chemistry*, vol. 13, No. 2, pp. 462-465, (1974).
Singhal, et al., "Drug Polymorphism and Dosage Form Design: A Practical Perspective," *Advanced Drug Delivery Reviews*, vol. 56, pp. 335-347, (2004).
Skoog, et al., *Principles of Instrumental Analysis*, Fourth Edition, pp. 577, (1992).
Smith, et al., "Oxford Dictionary of Biochemistry and Molecular Biology", *Oxford University Press*, pp. 145, (1997).
Snyder, et al., "Functional Profile of a Novel Modulator of Serotonin, Dopamine, and Glutamate Neurotransmission," *Psychopharmacology*, vol. 232, pp. 605-621, (2015); Published online Aug. 2014, DOI 10.1007/s00213-014-3704-1.
Southwick, et al., "Neuroendocrine Alterations in Posttraumatic Stress Disorder," *Psychiatric Annals Journal*, vol. 28, No. 8, pp. 436-442, (1998).
Sugahara, et al., "A Facile Copper-Catalyzed Ullman Condensation: N-Arylation of Heterocyclic Compounds Containing an—NHCO-Moiety," *Chem. Pharm. Bull.*, vol. 45, No. 4, pp. 719-721, (1997).
Taragano, et al., "A Double-Blind, Randomized, Fixed-Dose Trial of Fluoxetine vs. Amitriptyline in the Treatment of Major Depression Complicating Alzheimer's Disease," *Psychosomatics*, vol. 38, No. 3, pp. 246-252, (1997).
Tariot, et al., "Memantine Treatment in Patients with Moderate to Severe Alzheimer Disease Already Receiving Donepezil: A Randomized Controlled Trail," *JAMA*, vol. 291, No. 3, pp. 317-324, (2004).
Tonn, et al., "Simultaneous Analysis of Diphenhydramine and a Stable Isotope Analog ($^2H_{10}$)Diphenhydramine Using Capillary Gas Chromatography with Mass Selective Detection in Biological Fluids from Chronically Instrumented Pregnant Ewes," *Biological Mass Spectrometry*, vol. 22, pp. 633-642, (1993).
Tung, R., "The Development of Deuterium-Containing Drugs," *Innovations in Pharmaceutical Technology*, vol. 32, pp. 1-4, (2010).
Wagaw, et al., "A Palladium-Catalyzed Method for the Preparation of Indoles Via the Fischer Indole Synthesis," *Journal of the American Chemical Society*, vol. 121, No. 44, pp. 10251-10263, (1999).
Weschules, et al., "Acetylcholinesterase Inhibitor and N-Methyl-D- -Aspartic Acid Receptor Antagonist Use among Hospice Enrollees with a Primary Diagnosis of Dementia," *Journal of Palliative Medicine*, vol. 11, No. 5, pp. 738-745, (2008).
Wiese, M., "DSC Detection of Polymorphism in Pharmaceutical Anhydrous Dexamethasone Acetate," *TA Instruments*, TA 302, pp. 1-4, (2002).
Wolen, R. L., "The Application of Stable Isotopes to Studies of Drug Bioavailability and Bioequivalence," *J. Clin. Pharmacol.*, vol. 26, pp. 419-424, (1986).
Wolfe, et al., "An Improved Catalyst System for Aromatic Carbon-nitrogen Bond Formation: The Possible Involvement of Bis(Phosphine) Palladium Complexes as Key Intermediates," *J. Am. Chem. Soc.*, vol. 118, pp. 7215-7216, (1996).
Wolfe, et al., "Intramolecular Palladium-Catalyzed Aryl Amination and Aryl Amidation," *Tetrahedron*, vol. 52, No. 21, pp. 7525-7546, (1996).
Wolter, et al., "Synthesis of N-Aryl Hydrazides by Copper-Catalyzed Coupling of Hydrazides with Aryl Iodides," *Organic Letters*, vol. 3, No. 23, pp. 3803-3805, (2001).
Written Opinion of the International Searching Authority for International Application No. PCT/US2013/036514 dated Aug. 16, 2013, 4 pages.
Yamada, et al., "A Mild Copper-mediated Intramolecular Amination of Aryl Halides," *Synlett*, No. 2, pp. 231-234, (2002).
Yang, et al., "The Development of Efficient Protocols for the Palladium-catalyzed Cyclization Reactions of Secondary Amides and Carbamates," *Organic Letters*, vol. 1, No. 1, pp. 35-37, (1999).
Yudofsky, et al., "Propranolol in the Treatment of Rage and Violent Behavior in Patients with Chronic Brain Syndromes," *Am. J. Psychiatry*, vol. 138, No. 2, pp. 218-220, (1981).
Zhang, et al., "Highly Efficient Copper-catalyzed N-arylation of Alkylamines with Aryl Iodides Using Phosphoramidite as Ligand," *Catalysis Communications*, vol. 6, pp. 784-787, (2005).
Press Release, "Intra-Cellular Therapies Announces Additional Results from Phase I/II Clinical Trial for ITI-007 in Healthy Geriatric Subjects and Patients With Dementia," Intra-Cellular Therapies, Press Release Date: Nov. 21, 2014, (http://ir.intracellulartherapies.com/releasedetail.cfm?ReleaseID=884325), accessed on May 31, 2016.
Davis et al., "ITI-007: A Novel Treatment for Behavioral Disturbances Associated with Dementia and Related Disorders," Clinical Trials in Alzheimer's Disease (CTAD) Congress 2014 (2014) (poster presentation).
Davis et al., "Rationale for the Development of Low Doses of ITI-007 for the Treatment of Behavioral Disturbances Associated with Dementia," The Journal of Prevention of Alzheimer's Disease, 2(4):302 (2015) (Clinical Trials in Alzheimer's Disease (CTAD) Congress, Symposium Summary OC51).
Davis, et al., "Lumateperone (ITI-007), A Novel Drug in Development for the Treatment of Agitation in Patients with Dementia, including Alzheimer's Disease: Rationale and Clinical Design," The Journal of Prevention of Alzheimer's Disease, 4(4):372 (2017) (Clinical Trials in Alzheimer's Disease (CTAD) Congress, Symposium Summary P93.
Howland, R.H., "Deuterated Drugs," Journal of Psychosocial Nursing and Mental Health Services, 53(9): 13-16 (2015).
International Search Report issued in International Application No. PCT/US2017/054962, dated Nov. 27, 2017, 3 pages.
Marek et al. Synergistic Action of 5-HT2A Antagonists and Selective Serotonin Reuptake Inhibitors in Neuropsychiatric Disorders. Neuropsychopharmacology, 2003. vol. 28, pp. 402-412. (Year: 2003).
O'Gorman, et al., "Lumateperone (ITI-007): A Novel Investigational Agent with Broad Therapeutic Potential Across Multiple Neuropsychiatric Disorders," Poster P.1.g.038, European College of Neuropsychopharmacology (ECNP) Congress (2017).
Palanisamy, M. et al., "Cellulose-Based Matrix Microspheres of Prednisolone Inclusion Complex; Preparation and Characterization." American Association of Pharmaceutical Scientists PharmSciTech, vol. 12, No. 1, pp. 388-400, (2011).
Satlin, et al., "ITI-007 (Lumateperone) for the Treatment of Agitation in Patients with Dementia, including Alzheimer's Disease," Alzheimer's & Dementia 14(7) (Suppl.): P678-79 (2018) (Alzheimer's Assoc. International Conference 2018, summary of Poster P2-032).
Satlin, et al., "ITI-007 (Lumateperone) for the Treatment of Agitation in Patients with Dementia, including Alzheimer's Disease," Poster P2-032, Alzheimer's Assoc. International Conference 2018 (2018).
Timmins, G.S., "Deuterated drugs: where are we now?" Expert Opinion on Therapeutic Patents, 1-9 (2014).
Vanover, et al., "A Novel Approach to Address an Unmet Need in the Treatment of Schizophrenia and Depression: Lumateperone, an Innovative Modulator of Dopamine, Serotonin, and Glutamate," Abstract presented at the American Society of Clinical Psychopharmacology (ASCP) Annual Meeting; May 29-Jun. 1, 2018; Miami, FL.
Vanover, et al., "Dopamine D2 receptor occupancy of lumateperone (ITI-007): a Positron Emission Tomography Study in patients with schizophrenia," Neuropsychopharmacology 44:598-605, (2019).

(56) References Cited

OTHER PUBLICATIONS

Wennogle, et al., "Activation of NMDA and AMPA Receptors by Lumateperone (ITI-007): Implications for Antidepressant Activity," Abstract presented at the 2017 Collegium Internationale Neuro-Psychopharmacologicum (CINP) Thematic Meeting: Treatment Resistant Depression; Jul. 20-22, 2017; Prague.

Written Opinion of the International Searching Authority for International Application No. PCT/US2017/054962 dated Nov. 27, 2017, 8 pages.

TRANSMUCOSAL AND SUBCUTANEOUS COMPOSITIONS

This application claims priority to U.S. Provisional Application No. 62/476,538, filed Mar. 24, 2017, the contents of which are incorporated herein by reference in its entirety.

FIELD

This disclosure relates to certain novel transmucosal and subcutaneous pharmaceutical formulations comprising substituted heterocycle fused gamma-carbolines, the manufacture of such formulations, and methods of use thereof, e.g., in the treatment of diseases or abnormal conditions involving or mediated by the 5-HT$_{2A}$ receptor, serotonin transporter (SERT), and/or dopamine D$_1$/D$_2$ receptor signaling pathways. The invention includes methods of treatment and/or prophylaxis of diseases and disorders including, but not limited to, anxiety, psychosis, schizophrenia, sleep disorders, sexual disorders, migraine, conditions associated with cephalic pain, social phobias, gastrointestinal disorders such as dysfunction of the gastrointestinal tract motility and obesity; depression (including major depressive disorder (MDD)) and mood disorders associated with psychosis or Parkinson's disease; psychosis such as schizophrenia associated with depression; bipolar disorder (e.g., bipolar depression); and other psychiatric and neurological conditions, as well as to combinations with other agents

BACKGROUND 1-(4-fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one (sometimes referred to as 4-((6bR,10aS)-3-methyl-2,3,6b,9,10,10a-hexahydro-1H-pyrido[3',4':4,5]pyrrolo[1,2,3-de]quinoxalin-8(7H)-yl)-1-(4-fluorophenyl)-1-butanone, or as ITI-007), has the following structure:

Formula I

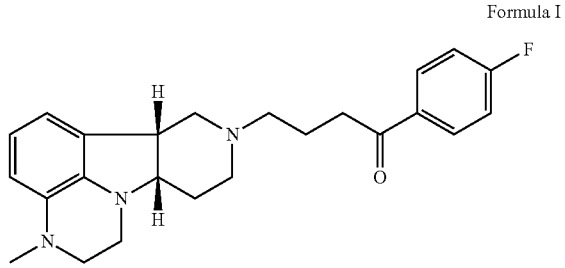 [SMILES: CN1CCN2c3c(cccc31)[C@@H]1CN(CCCC(=O)c3ccc(F)cc3)CC[C@@H]12]

The Compound of Formula I is a potent 5-HT$_{2A}$ receptor ligand (Ki=0.5 nM) with strong affinity for dopamine (DA) D2 receptors (K$_i$=32 nM) and the serotonin transporter (SERT) (K$_i$=26 nM, measured using 3H-imipramine binding displacement to human recombinant SERT), but negligible binding to receptors associated with cognitive and metabolic side effects of antipsychotic drugs (e.g., H1 histaminergic, 5-HT$_{2C}$, and muscarinic receptors). This compound is currently in clinical trials, i.e., for the treatment of schizophrenia, bipolar disorder and dementia including Alzheimer's disease. The Compound of Formula I, and analogs thereof, salts thereof, and methods of treatment comprising such compounds, and methods of manufacturing such compounds, have been disclosed, e.g., in U.S. Pat. Nos. 6,548,493; 7,238,690; 6,552,017; 6,713,471; 7,183,282; RE39,680; RE39,679; U.S. Patent Publications 2004/209864, 2010/113781, 2011/071080, 2011/112105, 2013/0202692, 2015/0079172, 2017/0183350; and PCT Publication WO 2017/165843 and WO 2017/117514. The contents of each of these U.S. patents, U.S. patent Publications, and PCT Publications are hereby incorporated by reference in their entireties.

Deuterated variants of ITI-007 are generally disclosed in US 2017/0183350 and WO 2017/165843. The deuterated compounds are designed to slow or inhibit in vivo metabolism by substituted deuterium atoms for hydrogen atoms of ITI-007 at molecular positions which are the target of metabolic activity. The natural metabolites of ITI-007 are pharmacologically active, but with somewhat different receptor selectivity profiles. These deuterated derivatives can therefore provide modified pharmacokinetic profiles owing to altered rates or pathways of metabolism, as well as modified overall pharmacological profile due to shifting the balance between active parent species and active metabolite species.

One such deuterated compound is 1-(4-fluoro-phenyl)-4-((6bR,10aS)-2,2-d$_2$-3-methyl-2,3,6b,9,10,10a-hexahydro-1H,7H-pyrido[3',4':4,5]pyrrolo[1,2,3-de]quinoxalin-8-yl)-butan-1-one, the Compound of Formula II:

Formula II

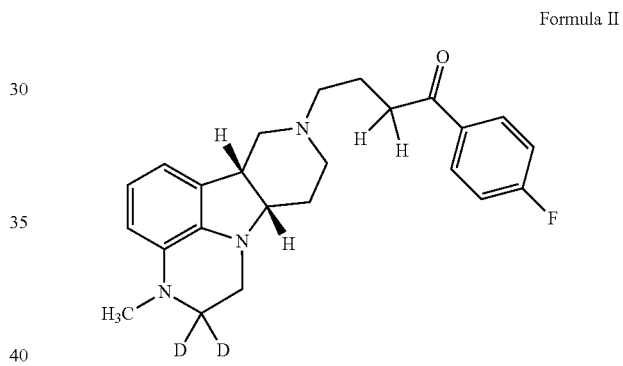

Another such deuterated compound is 1-(4-fluoro-phenyl)-4-((6bR,10 aS)-1,1,2,2-d$_4$-3-methyl-2,3,6b,9,10,10a-hexahydro-1H,7H-pyrido[3',4':4,5]pyrrolo[1,2,3-de]quinoxalin-8-yl)-butan-1-one, the Compound of Formula III:

Formula III

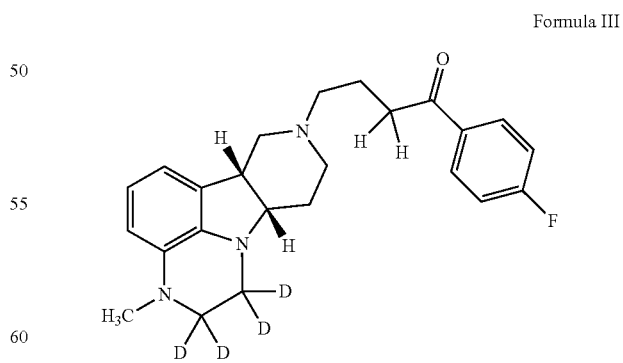

The Compounds of Formula I, II and Formula III each undergo significant first-pass metabolism in the liver. The high rate of metabolism requires the administration of higher oral doses of drug than would otherwise be needed, resulting in an increased burden on the liver, increased costs in manufacturing, difficulties in formulation and potentially higher patient-to-patient variability in dose response. There is therefore a need for new routes of administration that avoid first pass-metabolism, and which would result in correspondingly lower dosing requirements.

It has been disclosed that for a number of drugs transmucosal delivery, such as sublingual delivery, buccal delivery, and intranasal delivery, and subcutaneous delivery, are effective alternatives to traditional dosage forms such as parenteral and oral dosing. Parenteral (intravenous) dosing is very effective in avoiding first-pass metabolism, but is limited in its usefulness because it requires administration by trained professionals, usually in a clinical environment. In contrast, transmucosal delivery systems can be used to formulate drugs which can be taken by patients without professional supervision and can result in rapid drug absorption with minimal first-pass metabolism. Subcutaneous delivery similarly provides highly effective drug absorption with minimal first-pass metabolism, while also providing the potential for delayed or extended release (compared to IV administration).

The use of transmucosal drug delivery formulations is well known, with sublingual formulations of nitroglycerin dating back to 1847. These formulations involve the transfer of active drug agent across mucosal membranes, including the oral mucosa, nasal mucosa, and the vaginal mucosa. These mucosal surface are much more permeable to drugs than the skin (keratinized epithelium) and have similar permeability as the gastrointestinal mucosa, but without the problem that GI absorption of drugs results in immediate passage to the liver for metabolism. Oral mucosal delivery systems include buccal and sublingual systems.

Existing transmucosal delivery systems include rapidly-disintegrating tablets and wafers, thin, dissolvable films, aerosol sprays, dissolvable gels, as well as aqueous solutions. Examples of dissolvable film delivery systems include those disclosed in U.S. Pat. No. 4,136,145 to Fuchs, U.S. Pat. No. 4,849,246 to Schmidt, U.S. Pat. No. 5,629,003 to Horstmann, U.S. Pat. No. 5,948,430 to Zerbe, U.S. Pat. No. 9,108,340 to Yang, U.S. Pat. No. 8,906,277 to Yang, U.S. Pat. No. 8,900,498 to Yang, U.S. Pat. No. 8,900,497 to Yang, U.S. Pat. No. 8,652,378 to Yang, U.S. Pat. No. 8,603,514 to Yang, U.S. Pat. No. 9,427,412 to Bryson, and U.S. Pat. No. 8,414,922 to Bryson. Other transmucosal systems are disclosed in U.S. Pat. No. 5,763,476 to Delbressine (sublingual and buccal solutions and solids), U.S. Pat. No. 9,216,175 to Amancha (sublingual spray), U.S. Pat. No. 8,835,459 to Kottayil (sublingual spray), and U.S. Pat. No. 6,552,024 to Chen (various mucosal delivery systems). Some drugs, however, such as apomorphine, are found to be tolerated and effective in some transmucosal delivery forms, but not in others (see U.S. Pat. No. 9,427,412, describing lack of efficacy or tolerability for sublingual tablets and intranasal sprays, but not for sublingual films). In addition, individual formulations must be fine-tuned to particular active pharmaceutical ingredients to ensure reliability in delivery. Thus, while the field of transmucosal drug delivery has a long history, considerably effort is required in adapting any selected transmucosal delivery technology to a particular active pharmaceutical ingredient.

Subcutaneous injection is also well-known in the art, and is popularly used for the administration of insulin, morphine, methotrexate and many other drugs and vaccines. Subcutaneous injection is often performed by physicians and other medical personally using traditional syringes with small gauge needles, but there also exists many specialty devices for patient self-administration of subcutaneous injection, such as pre-filled syringes, auto-injectors, and wearable injectors. Such devices include the HumatroPen for insulin injection (Eli Lilly, Indianapolis, Ind., U.S.) and the Otrexup auto-injector for methotrexate injection (Antares Pharma, Ewing, N.J., U.S.).

There is a need for improved pharmaceutical delivery systems for the safe, effective, reliable delivery of the Compounds for Formula I and/or the Compound of Formula II. The present disclosure provides novel transmucosal and subcutaneous formulations for the delivery of these compounds without the drawbacks of existing parenteral and oral delivery systems.

BRIEF SUMMARY

The present disclosure is directed to novel transmucosal and subcutaneous pharmaceutical formulations comprising 1-(4-fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one, as well as deuterated variants thereof, in free base, co-crystal or salt forms. Transmucosal formulations include, but are not limited to, oral, nasal, and vaginal formulations in liquid, solid and/or aerosol forms, including, sublingual, buccal, intranasal and intravaginal tablets, wafers, films, sprays and gels.

Further areas of applicability of the present invention will become apparent from the detailed description provided hereinafter. It should be understood that the detailed description and specific examples, while indicating preferred embodiments of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material in free base equivalent form.

In a first embodiment, the present disclosure provides a transmucosal pharmaceutical formulation (Formulation 1) comprising 1-(4-fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one (Compound of Formula I), in free base, co-crystal or salt form. The present disclosure further provides the following Formulations:

1.1. Formulation 1, wherein the formulation comprises the Compound of Formula I in free base form.
1.2. Formulation 1, wherein the formulation comprises the Compound of Formula I in salt form, e.g., in pharmaceutically acceptable salt form, optionally in amorphous solid or crystal salt form; or in co-crystal form, e.g., in nicotinamide or isonicotinamide co-crystal form.

1.3. Formulation 1.2, wherein the salt form is a tosylate, oxalate, cyclamate, 4-aminosalicylate, or hydrochloride salt form, optionally, wherein said salt form is a crystal salt form.

1.4. Any preceding formulation, wherein the formulation comprises from 0.01 to 100 mg of the Compound of Formula I (free base equivalent), e.g., 0.01 to 75 mg, 0.01 to 50 mg, 0.01 to 30 mg, 0.01 to 20 mg, 0.1 to 20 mg, 5 to 20 mg, 10 to 20 mg, 10 to 30 mg, 20 to 30 mg, 20 to 50 mg, or 50 to 100 mg.

1.5. Any preceding formulation, wherein the formulation comprises from 0.01 to 10 mg of the Compound of Formula I (free base equivalent).

1.6. Any preceding formulation, wherein the formulation comprises from 0.05 to 8 mg of the Compound of Formula I (free base equivalent), e.g., from 0.1 to 5 mg, or from to 5 to 10 mg.

1.7. Any preceding formulation, further comprising one or more hydrophilic water-soluble or water swellable polymers.

1.8. Formula 1.7, wherein the polymer is selected from the group consisting of natural or modified cellulosic polymers, polymers of ethylene oxide and/or propylene oxide, polymers comprising acrylic acid monomers, natural or modified gums (e.g. xanthan gum), natural or modified starches (e.g., pre-gelatinized starches), or any mixture thereof.

1.9. Any preceding formulation, further comprising a hydrophobic polymer or poorly water soluble polymer, for example, a silicone polymer, or polyalkylene polymer (e.g., polyethylene).

1.10. Any preceding formulation, further comprising one or more excipients selected from the group consisting of plasticizers, surfactants, drying agents, flavors, sweeteners, binders, disintegrants, humectants (e.g., polyols), wetting agents, antioxidants, buffering agents (e.g., acids, bases and/or salts thereof), and thickening agents (e.g., gelling agents).

1.11. Formula 1.10, wherein the one or more excipients are selected from any of the following: alcohols (ethanol, glycerol, propylene glycol), gums (e.g., acacia, guar, agar, xanthan, tragacanth, karaya, gellan), polysaccharides and polysaccharide derivatives (e.g., starches, dextrans, pectins, alginates, carrageenans, cellulose, cellulose derivatives (e.g., carboxymethyl cellulose, methylcellulose, hydroxyalkyl celluloses (e.g., hydroxyethyl cellulose, hydroxypropyl cellulose, hydroxypropyl methyl cellulose)), gelatins including non-gelling and gelling types (e.g., mammalian gelatins such as bovine gelatin, porcine gelatins, avian gelatins, fish gelatins (e.g., mixed high molecular weight and low molecular weight gelatins), synthetic polymers (e.g., polyvinylpyrrolidones, polyethylene oxide and/or polypropylene oxide polymers and copolymers (e.g., poloxamers, such as poloxamer 188), polyacrylate polymers (e.g., carbopols), polyamide polymers), sugars and sugar alcohols (e.g., dextrose, lactose, galactose, glucose, ribose, sucrose, trehalose, mannitol, maltitol, lactitol, sorbitol, xylitol, erythritol, galactitol, inositol) polypeptides/proteins, amino acids, inorganic or organic acids (e.g., citric acid, lactic acid, malic acid, gluconic acid, benzoic acid, toluenesulfonic acid, phosphoric acid, sulfuric acid, hydrochloric acid, tartaric acid, oxalic acid, cyclamic acid, ascorbic acid, methanesulfonic acid, benzenesulfonic acid, formic acid) and their salts (e.g., sodium, potassium, calcium, magnesium, lithium, ammonium salts of aforementioned acids), inorganic or organic bases (e.g., alkali metal or alkaline earth metal carbonates, bicarbonates, hydroxide, oxides), anionic surfactants (e.g., sodium lauryl sulfate, sodium laureth sulfate, sodium dodecylbenzenesulfonate, sodium lauroyl sarcosinate, sodium stearate), cationic surfactants (e.g., benzalkonium halides, cetylpyridinium halides, cetrimonium halides, benzethonium halides), zwitterionic surfactants (e.g., cocamidoalkyl betaines, such as cocamidopropyl betaine), nonionic surfactants (e.g., fatty alcohol ethoxylates (e.g., polyethylene glycol polydodecyl ethers), sorbitan esters (e.g., sorbitan monolaurate, sorbitan monooleate, sorbitan monopalmitate, sorbitan monostearate, sorbitan tristearate), polyethoxylated sorbitan esters (e.g., polysorbate 20, polysorbate 40, polysorbate 60, polysorbate 80), and antioxidants (e.g., ascorbic acid, sodium metabisulfite, BHT, BHA, TBHQ, propyl gallate, beta-carotene, tocopherols, tocotrienols).

1.12. Formula 1.11, wherein any one or more of said excipients are present in an amount of 0.01 to 20% by weight of the formulation, e.g., 0.01 to 15%, or 0.01 to 10%, or 0.1 to 20%, or 0.1 to 15% or 0.1 to 10%, or 0.5 to 10%, or 0.5 to 5%, or 1 to 5%, or 2.5 to 5%, or 1 to 3%, or 0.1 to 1%.

1.13. Any preceding formulation which is free of added plasticizer, surfactant or humectant (e.g., polyol).

1.14. Any preceding formulation, wherein the formulation comprises from 0.01 to 99% water, for example, from 0.01 to 10% water, or from 0.01 to 5% water, or from 50 to 99% water, or from 75 to 99% water, or from 25 to 75% water.

1.15. Any preceding formulation, wherein the formulation is a rapidly dissolving tablet or wafer, e.g., a sublingual tablet or wafer.

1.16. Any of formulations 1 or 1.1 to 1.14, wherein the formulation is an oral spray, e.g., a sublingual spray or buccal spray.

1.17. Any of formulations 1 or 1.1 to 1.14, wherein the formulation is a rapidly dissolving film, e.g., a sublingual film or buccal film.

1.18. Formulation 1.17, wherein the film is a single layer or multi-layer film.

1.19. Formulation 1.17 or 1.18, wherein the film has uniform or substantially uniform thickness.

1.20. Formulation 1.17, 1.18 or 1.19 wherein the Compound of Formula I is uniformly or substantially uniformly distributed throughout the film.

1.21. Any of formulations 1 or 1.1 to 1.14, wherein the formulation is an intranasal spray.

1.22. Any of formulations 1 or 1.1 to 1.14, wherein the formulation is an oral gel, e.g., a rapidly dissolving sublingual or buccal gel.

1.23. Any of formulations 1 or 1.1 to 1.14, wherein the formulation is an intravaginal formulation, e.g., an intravaginal rapidly dissolving tablet, wafer or gel, or an intravaginal spray or an intravaginal rapidly dissolving film.

1.24. Any preceding formulation wherein the Compound of Formula I is incorporated into the formulation as microparticles (e.g., particles having an average diameter of less than 50 μm, less than 30 μm, less than 10 μm, or less than 5 μm, or less than 1 μm).

1.25. Any preceding formulation wherein the Compound of Formula I is incorporated into the formulation as nanoparticles (e.g., particles having an average diameter of less than 100 nm, or less than 50 nm, or less than 10 nm).

1.26. Any preceding formulation, wherein the formulation is absorbed by the mucosa (e.g., dissolves) in less than 30 seconds after administration.

1.27. Any preceding formulation, wherein the dosage of the Compound of Formula I is from 1 to 20% of the unit daily dosage for oral administration, for example, 5 to 15% of the oral dosage.

1.28. Any preceding formulation, wherein the formulation further comprises the Compound of Formula II or the Compound of Formula III or a combination thereof.

1.29. Any preceding formulation, wherein the formulation is formulated for administration once per day, or twice per day, or three times per day, or four times per day, or once every two days, or once every three days.

1.30. Any preceding formulation, wherein the formulation comprises the Compound of Formula I in tosylate salt form, e.g., in mono-tosylate salt form or di-tosylate salt form, or a mixture thereof.

1.31. Formulation 1.30, wherein the formulation further comprises toluenesulfonic acid, e.g., wherein the formulation comprises the Compound of Formula I in tosylate salt form and toluenesulfonic acid in a ratio of 1:3 to 3:1, or 1:2 to 2:1 or 1:1.5 to 1.5:1, or about 1:1.

1.32. Any preceding formulation, wherein the Compound of Formula I is enriched in deuterium at one or more hydrogen atom positions, for example, wherein at any one or more hydrogen atom positions there is substantially greater than the natural level of incorporation of deuterium at such positions of the structure (e.g., greater than 0.1%, or greater than 0.5%, or greater than 1%, or greater than 5%).

1.33. Formulation 1.32, wherein the Compound of Formula I has greater than 50% incorporation of deuterium at any one or more hydrogen atom positions of the structure (i.e., greater than 50 atom % D), e.g., greater than 60%, or greater than 70%, or greater than 80%, or greater than 90% or greater than 95%, or greater than 96%, or greater than 97%, or greater than 98%, or greater than 99%.

1.34. Any of formulations 1 or 1.1 to 1.31, wherein all hydrogen atom positions of the Compound of Formula I are non-enriched in deuterium (i.e., every hydrogen atom position contains the natural abundance of deuterium or less than 0.1% deuterium).

In a second embodiment, the present disclosure provides a transmucosal pharmaceutical formulation (Formulation 2) comprising 1-(4-fluoro-phenyl)-4-((6bR,10aS)-2,2-$d_2$-3-methyl-2,3,6b,9,10,10a-hexahydro-1H,7H-pyrido[3',4':4,5]pyrrolo[1,2,3-de]quinoxalin-8-yl)-butan-1-one (Compound of Formula II), in free base, co-crystal or salt form. The present disclosure further provides the following Formulations:

2.1. Formulation 2, wherein the formulation comprises the Compound of Formula II in free base form.

2.2. Formulation 2, wherein the formulation comprises the Compound of Formula II in salt form, e.g., in pharmaceutically acceptable salt form, optionally in amorphous solid or crystal salt form; or in co-crystal form, e.g., in nicotinamide or isonicotinamide co-crystal form.

2.3. Formulation 2.2, wherein the salt form is a tosylate, oxalate, cyclamate, 4-aminosalicylate, or hydrochloride salt form, optionally, wherein said salt form is a crystal salt form.

2.4. Any preceding formulation, wherein the formulation comprises from 0.01 to 100 mg of the Compound of Formula II (free base equivalent), e.g., 0.01 to 75 mg, 0.01 to 50 mg, 0.01 to 30 mg, 0.01 to 20 mg, 0.1 to 20 mg, 5 to 20 mg, 10 to 20 mg, 10 to 30 mg, 20 to 30 mg, 20 to 50 mg, or 50 to 100 mg.

2.5. Any preceding formulation, wherein the formulation comprises from 0.01 to 10 mg of the Compound of Formula II (free base equivalent).

2.6. Any preceding formulation, wherein the formulation comprises from 0.05 to 8 mg of the Compound of Formula II (free base equivalent), e.g., from 0.1 to 5 mg, or from to 5 to 10 mg.

2.7. Any preceding formulation, further comprising one or more hydrophilic water-soluble or water swellable polymers.

2.8. Formula 2.7, wherein the polymer is selected from the group consisting of natural or modified cellulosic polymers, polymers of ethylene oxide and/or propylene oxide, polymers comprising acrylic acid monomers, natural or modified gums (e.g. xanthan gum), natural or modified starches (e.g., pre-gelatinized starches), or any mixture thereof.

2.9. Any preceding formulation, further comprising a hydrophobic polymer or poorly water soluble polymer, for example, a silicone polymer, or polyalkylene polymer (e.g., polyethylene).

2.10. Any preceding formulation, further comprising one or more excipients selected from the group consisting of plasticizers, surfactants, drying agents, flavors, sweeteners, binders, disintegrants, humectants (e.g., polyols), wetting agents, antioxidants, buffering agents (e.g., acids, bases and/or salts thereof), and thickening agents (e.g., gelling agents).

2.11. Formula 2.10, wherein the one or more excipients are selected from any of the following: alcohols (ethanol, glycerol, propylene glycol), gums (e.g., acacia, guar, agar, xanthan, tragacanth, karaya, gellan), polysaccharides and polysaccharide derivatives (e.g., starches, dextrans, pectins, alginates, carrageenans, cellulose, cellulose derivatives (e.g., carboxymethyl cellulose, methylcellulose, hydroxyalkyl celluloses (e.g., hydroxyethyl cellulose, hydroxypropyl cellulose, hydroxypropylmethyl cellulose)), gelatins including non-gelling and gelling types (e.g., mammalian gelatins such as bovine gelatin, porcine gelatins, avian gelatins, fish gelatins (e.g., mixed high molecular weight and low molecular weight gelatins), synthetic polymers (e.g., polyvinylpyrrolidones, polyethylene oxide and/or polypropylene oxide polymers and copolymers (e.g., poloxamers, such as poloxamer 188), polyacrylate polymers (e.g., carbopols), polyamide polymers), sugars and sugar alcohols (e.g., dextrose, lactose, galactose, glucose, ribose, sucrose, trehalose, mannitol, maltitol, lactitol, sorbitol, xylitol, erythritol, galactitol, inositol) polypeptides/proteins, amino acids, inorganic or organic acids (e.g., citric acid, lactic acid, malic acid, gluconic acid, benzoic acid, toluenesulfonic acid, phosphoric acid, sulfuric acid, hydrochloric acid, tartaric acid, oxalic acid, cyclamic acid, ascorbic acid, methanesulfonic acid, benzenesulfonic acid, formic acid) and their salts (e.g., sodium, potassium, calcium, magnesium, lithium, ammonium salts of aforementioned acids), inorganic or organic bases (e.g., alkali metal or alkaline earth metal carbonates, bicarbonates, hydroxide, oxides), anionic surfactants (e.g., sodium lauryl sulfate, sodium laureth sulfate, sodium dodecylbenzenesulfonate, sodium lauroyl sarcosinate, sodium stearate), cationic surfactants (e.g., benzalkonium halides, cetylpyridinium halides, cetrimonium halides, benzethonium halides), zwitterionic surfactants (e.g., cocamidoalkyl betaines, such as cocamidopropyl betaine), nonionic surfactants (e.g., fatty alcohol ethoxylates (e.g., polyethylene glycol polydodecyl ethers), sorbitan esters (e.g., sorbitan monolaurate, sorbitan monooleate, sorbitan monopalmitate, sorbitan monostearate, sorbitan tristearate), polyethoxylated sorbitan esters (e.g., polysorbate 20, polysorbate 40, polysorbate 60, polysorbate 80), and antioxidants (e.g., ascorbic acid, sodium metabisulfite, BHT, BHA, TBHQ, propyl gallate, beta-carotene, tocopherols, tocotrienols).

2.12. Formula 2.11, wherein any one or more of said excipients are present in an amount of 0.01 to 20% by weight of the formulation, e.g., 0.01 to 15%, or 0.01 to 10%, or 0.1 to 20%, or 0.1 to 15% or 0.1 to 10%, or 0.5 to 10%, or 0.5 to 5%, or 1 to 5%, or 2.5 to 5%, or 1 to 3%, or 0.1 to 1%.

2.13. Any preceding formulation which is free of added plasticizer, surfactant or humectant (e.g., polyol).

2.14. Any preceding formulation, wherein the formulation comprises from 0.01 to 99% water, for example, from 0.01 to 10% water, or from 0.01 to 5% water, or from 50 to 99% water, or from 75 to 99% water, or from 25 to 75% water.

2.15. Any preceding formulation, wherein the formulation is a rapidly dissolving tablet or wafer, e.g., a sublingual tablet or wafer.

2.16. Any of formulations 2 or 2.1 to 2.14, wherein the formulation is an oral spray, e.g., a sublingual spray or buccal spray.

2.17. Any of formulations 2 or 2.1 to 2.14, wherein the formulation is a rapidly dissolving film, e.g., a sublingual film or buccal film.

2.18. Formulation 2.17, wherein the film is a single layer or multi-layer film.

2.19. Formulation 2.17 or 2.18, wherein the film has uniform or substantially uniform thickness.

2.20. Formulation 2.17, 2.18 or 2.19 wherein the Compound of Formula II is uniformly or substantially uniformly distributed throughout the film.

2.21. Any of formulations 2 or 2.1 to 2.14, wherein the formulation is an intranasal spray.

2.22. Any of formulations 2 or 2.1 to 2.14, wherein the formulation is an oral gel, e.g., a rapidly dissolving sublingual or buccal gel.

2.23. Any of formulations 2 or 2.1 to 2.14, wherein the formulation is an intravaginal formulation, e.g., an intravaginal rapidly dissolving tablet, wafer or gel, or an intravaginal spray or an intravaginal rapidly dissolving film.

2.24. Any preceding formulation wherein the Compound of Formula II is incorporated into the formulation as microparticles (e.g., particles having an average diameter of less than 50 μm, less than 30 μm, less than 10 μm, or less than 5 μm, or less than 1 μm).

2.25. Any preceding formulation wherein the Compound of Formula II is incorporated into the formulation as nanoparticles (e.g., particles having an average diameter of less than 100 nm, or less than 50 nm, or less than 10 nm).

2.26. Any preceding formulation, wherein the formulation is absorbed by the mucosa (e.g., dissolves) in less than 30 seconds after administration.

2.27. Any preceding formulation, wherein the dosage of the Compound of Formula II is from 1 to 20% of the unit daily dosage for oral administration, for example, 5 to 15% of the oral dosage.

2.28. Any preceding formulation, wherein the formulation further comprises the Compound of Formula I or the Compound of Formula III or a combination thereof.

2.29. Any preceding formulation, wherein the formulation is formulated for administration once per day, or twice per day, or three times per day, or four times per day, or once every two days, or once every three days.

2.30. Any preceding formulation, wherein the formulation comprises the Compound of Formula II in tosylate salt form, e.g., in mono-tosylate salt form or di-tosylate salt form, or a mixture thereof.

2.31. Formulation 2.30, wherein the formulation further comprises toluenesulfonic acid, e.g., wherein the formulation comprises the Compound of Formula II in tosylate salt form and toluenesulfonic acid in a ratio of 1:3 to 3:1, or 1:2 to 2:1 or 1:1.5 to 1.5:1, or about 1:1.

In a third embodiment, the present disclosure provides a subcutaneous pharmaceutical formulation (Formulation 3) comprising 1-(4-fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one (Compound of Formula I), in free base, co-crystal or salt form. The present disclosure further provides the following Formulations:

3.1. Formulation 3, wherein the formulation comprises the Compound of Formula I in free base form.

3.2. Formulation 3, wherein the formulation comprises the Compound of Formula I in salt form, e.g., in pharmaceutically acceptable salt form, optionally in amorphous solid or crystal salt form; or in co-crystal form, e.g., in nicotinamide or isonicotinamide co-crystal form.

3.3. Formulation 3.2, wherein the salt form is a tosylate, oxalate, cyclamate, 4-aminosalicylate, or hydrochloride salt form, optionally, wherein said salt form is a crystal salt form.

3.4. Any preceding formulation, wherein the formulation comprises from 0.01 to 100 mg of the Compound of Formula I (free base equivalent), e.g., 0.01 to 75 mg, 0.01 to 50 mg, 0.01 to 30 mg, 0.01 to 20 mg, 0.1 to 20 mg, 5 to 20 mg, 10 to 20 mg, 10 to 30 mg, 20 to 30 mg, 20 to 50 mg, or 50 to 100 mg.

3.5. Any preceding formulation, wherein the formulation comprises from 0.01 to 10 mg of the Compound of Formula I (free base equivalent).

3.6. Any preceding formulation, wherein the formulation comprises from 0.05 to 8 mg of the Compound of Formula I (free base equivalent), e.g., from 0.1 to 5 mg, or from to 5 to 10 mg.

3.7. Any preceding formulation, further comprising one or more of water, water soluble-polymers (e.g., modified celluloses, polyvinylpyrrolidones, polyethylene glycols), water-miscible alcohols (e.g., ethanol, glycerin and propylene glycol), bulking agents (e.g., sugars, sugar alcohols, and amino acids), inorganic salts (e.g. sodium chloride, calcium chloride, potassium chloride), buffers (e.g., carbonate and bicarbonate salts, citrate salts, phosphate salts, Tris salts), preservatives, antioxidants, chelating agents, and mixtures thereof.

3.8. Any preceding formulation, wherein the formulation comprises from 0.01 to 99% water, for example, from 0.01 to 10% water, or from 0.01 to 5% water, or from 50 to 99% water, or from 75 to 99% water, or from 25 to 75% water.

3.9. Any preceding formulation, wherein a substantial amount (e.g., greater than 75% or greater than 85%, or greater than 90%) of the Compound of Formula I is absorbed immediately (e.g., in less than 1 minute, or less than 5 minutes).

3.10. Any preceding formulation, wherein a significant amount (e.g., greater than 25%, or greater than 50% or greater than 75%) of the Compound of Formula I is not absorbed immediately (e.g., in greater than 5 minutes, or greater than 10 minutes, or greater than 30 minutes, or greater than 1 hour, or greater than 5 hours).

3.11. Any preceding formulation, wherein the formulation is packaged for use in a pre-filled syringe, a pre-filled auto-injector, or a sealed vial or similar container.

3.12. Any preceding formulation, wherein the formulation is packaged for use as a dry solid, e.g., a lyophilized solid, for reconstitution in a pharmaceutically acceptable solvent (e.g., sterile water for injection) at the point of use.

3.13. Any preceding formulation, wherein the dosage of the Compound of Formula I is from 1 to 20% of the unit daily dosage for oral administration, for example, 5 to 15% of the oral dosage.

3.14. Any preceding formulation, wherein the formulation further comprises the Compound of Formula II or the Compound of Formula III or a combination thereof.

3.15. Any preceding formulation, wherein the formulation is formulated for administration once per day, or once every two days, or once every three days, or once per week, or once every two weeks, or once every three weeks, or once per month, or once every two months, or once every three months, or once every six months.

3.16. Any preceding formulation, wherein the formulation comprises the Compound of Formula I in tosylate salt form, e.g., in mono-tosylate salt form or di-tosylate salt form, or a mixture thereof.

3.17. Formulation 3.16, wherein the formulation further comprises toluenesulfonic acid, e.g., wherein the formulation comprises the Compound of Formula I in tosylate salt form and toluenesulfonic acid in a ratio of 1:3 to 3:1, or 1:2 to 2:1 or 1:1.5 to 1.5:1, or about 1:1.

3.18. Any preceding formulation, wherein the Compound of Formula I is enriched in deuterium at one or more hydrogen atom positions, for example, wherein at any one or more hydrogen atom positions there is substantially greater than the natural level of incorporation of deuterium at such positions of the structure (e.g., greater than 0.1%, or greater than 0.5%, or greater than 1%, or greater than 5%).

3.19. Formulation 3.18, wherein the Compound of Formula I has greater than 50% incorporation of deuterium at any one or more hydrogen atom positions of the structure (i.e., greater than 50 atom % D), e.g., greater than 60%, or greater than 70%, or greater than 80%, or greater than 90% or greater than 95%, or greater than 96%, or greater than 97%, or greater than 98%, or greater than 99%.

3.20. Any of formulations 3 or 3.1 to 3.17, wherein all hydrogen atom positions of the Compound of Formula I are non-enriched in deuterium (i.e., every hydrogen atom position contains the natural abundance of deuterium or less than 0.1% deuterium).

In a fourth embodiment, the present disclosure provides a subcutaneous pharmaceutical formulation (Formulation 4) comprising 1-(4-fluoro-phenyl)-4-((6bR,10aS)-2,2-$d_2$-3-methyl-2,3,6b,9,10,10a-hexahydro-1H,7H-pyrido[3',4':4,5]pyrrolo[1,2,3-de]quinoxalin-8-yl)-butan-1-one (Compound of Formula II), in free base, co-crystal or salt form. The present disclosure further provides the following Formulations:

4.1. Formulation 4, wherein the formulation comprises the Compound of Formula II in free base form.

4.2. Formulation 4, wherein the formulation comprises the Compound of Formula II in salt form, e.g., in pharmaceutically acceptable salt form, optionally in amorphous solid or crystal salt form; or in co-crystal form, e.g., in nicotinamide or isonicotinamide co-crystal form.

4.3. Formulation 4.2, wherein the salt form is a tosylate, oxalate, cyclamate, 4-aminosalicylate, or hydrochloride salt form, optionally, wherein said salt form is a crystal salt form.

4.4. Any preceding formulation, wherein the formulation comprises from 0.01 to 100 mg of the Compound of Formula II (free base equivalent), e.g., 0.01 to 75 mg, 0.01 to 50 mg, 0.01 to 30 mg, 0.01 to 20 mg, 0.1 to 20 mg, 5 to 20 mg, 10 to 20 mg, 10 to 30 mg, 20 to 30 mg, 20 to 50 mg, or 50 to 100 mg.

4.5. Any preceding formulation, wherein the formulation comprises from 0.01 to 10 mg of the Compound of Formula II (free base equivalent).

4.6. Any preceding formulation, wherein the formulation comprises from 0.05 to 8 mg of the Compound of Formula II (free base equivalent), e.g., from 0.1 to 5 mg, or from to 5 to 10 mg.

4.7. Any preceding formulation, further comprising one or more of water, water soluble-polymers (e.g., modified celluloses, polyvinylpyrrolidones, polyethylene glycols), water-miscible alcohols (e.g., ethanol, glycerin and propylene glycol), bulking agents (e.g., sugars, sugar alcohols, and amino acids), inorganic salts (e.g. sodium chloride, calcium chloride, potassium chloride), buffers (e.g., carbonate and bicarbonate salts, citrate salts, phosphate salts, Tris salts), preservatives, antioxidants, chelating agents, and mixtures thereof.

4.8. Any preceding formulation, wherein the formulation comprises from 0.01 to 99% water, for example, from 0.01 to 10% water, or from 0.01 to 5% water, or from 50 to 99% water, or from 75 to 99% water, or from 25 to 75% water.

4.9. Any preceding formulation, wherein a substantial amount (e.g., greater than 75% or greater than 85%, or greater than 90%) of the Compound of Formula II is absorbed immediately (e.g., in less than 1 minute, or less than 5 minutes).

4.10. Any preceding formulation, wherein a significant amount (e.g., greater than 25%, or greater than 50% or greater than 75%) of the Compound of Formula II is not absorbed immediately (e.g., in greater than 5 minutes, or greater than 10 minutes, or greater than 30 minutes, or greater than 1 hour, or greater than 5 hours).

4.11. Any preceding formulation, wherein the formulation is packaged for use in a pre-filled syringe, a pre-filled auto-injector, or a sealed vial or similar container.

4.12. Any preceding formulation, wherein the formulation is packaged for use as a dry solid, e.g., a lyophilized solid, for reconstitution in a pharmaceutically acceptable solvent (e.g., sterile water for injection) at the point of use.

4.13. Any preceding formulation, wherein the dosage of the Compound of Formula II is from 1 to 20% of the unit daily dosage for oral administration, for example, 5 to 15% of the oral dosage.

4.14. Any preceding formulation, wherein the formulation further comprises the Compound of Formula I or the Compound of Formula III or a combination thereof.

4.15. Any preceding formulation, wherein the formulation is formulated for administration once per day, or once every two days, or once every three days, or once per week, or once every two weeks, or once every three weeks, or once per month, or once every two months, or once every three months, or once every six months.

4.16. Any preceding formulation, wherein the formulation comprises the Compound of Formula II in tosylate salt form, e.g., in mono-tosylate salt form or di-tosylate salt form, or a mixture thereof.

4.17. Formulation 4.16, wherein the formulation further comprises toluenesulfonic acid, e.g., wherein the formulation comprises the Compound of Formula II in tosylate salt form and toluenesulfonic acid in a ratio of 1:3 to 3:1, or 1:2 to 2:1 or 1:1.5 to 1.5:1, or about 1:1.

In a fifth embodiment, the present disclosure provides a transmucosal pharmaceutical formulation (Formulation 5) comprising 1-(4-fluoro-phenyl)-4-((6bR,10aS)-1,1,2,2-$d_4$-3-methyl-2,3,6b,9,10,10a-hexahydro-1H,7H-pyrido[3',4':4,5]pyrrolo[1,2,3-de]quinoxalin-8-yl)-butan-1-one (Compound of Formula III), in free base, co-crystal or salt form. The present disclosure further provides the following Formulations:

5.1. Formulation 5, wherein the formulation comprises the Compound of Formula III in free base form.

5.2. Formulation 5, wherein the formulation comprises the Compound of Formula III in salt form, e.g., in pharmaceutically acceptable salt form, optionally in amorphous solid or crystal salt form; or in co-crystal form, e.g., in nicotinamide or isonicotinamide co-crystal form.

5.3. Formulation 5.2, wherein the salt form is a tosylate, oxalate, cyclamate, 4-aminosalicylate, or hydrochloride salt form, optionally, wherein said salt form is a crystal salt form.

5.4. Any preceding formulation, wherein the formulation comprises from 0.01 to 100 mg of the Compound of Formula III (free base equivalent), e.g., 0.01 to 75 mg, 0.01 to 50 mg, 0.01 to 30 mg, 0.01 to 20 mg, 0.1 to 20 mg, 5 to 20 mg, 10 to 20 mg, 10 to 30 mg, 20 to 30 mg, 20 to 50 mg, or 50 to 100 mg.

5.5. Any preceding formulation, wherein the formulation comprises from 0.01 to 10 mg of the Compound of Formula III (free base equivalent).

5.6. Any preceding formulation, wherein the formulation comprises from 0.05 to 8 mg of the Compound of Formula III (free base equivalent), e.g., from 0.1 to 5 mg, or from to 5 to 10 mg.

5.7. Any preceding formulation, further comprising one or more hydrophilic water-soluble or water swellable polymers.

5.8. Formula 51.7, wherein the polymer is selected from the group consisting of natural or modified cellulosic polymers, polymers of ethylene oxide and/or propylene oxide, polymers comprising acrylic acid monomers, natural or modified gums (e.g. xanthan gum), natural or modified starches (e.g., pre-gelatinized starches), or any mixture thereof.

5.9. Any preceding formulation, further comprising a hydrophobic polymer or poorly water-soluble polymer, for example, a silicone polymer, or polyalkylene polymer (e.g., polyethylene).

5.10. Any preceding formulation, further comprising one or more excipients selected from the group consisting of plasticizers, surfactants, drying agents, flavors, sweeteners, binders, disintegrants, humectants (e.g., polyols), wetting agents, antioxidants, buffering agents (e.g., acids, bases and/or salts thereof), and thickening agents (e.g., gelling agents).

5.11. Formula 5.10, wherein the one or more excipients are selected from any of the following: alcohols (ethanol, glycerol, propylene glycol), gums (e.g., acacia, guar, agar, xanthan, tragacanth, karaya, gellan), polysaccharides and polysaccharide derivatives (e.g., starches, dextrans, pectins, alginates, carrageenans, cellulose, cellulose derivatives (e.g., carboxymethyl cellulose, methylcellulose, hydroxyalkyl celluloses (e.g., hydroxyethyl cellulose, hydroxypropyl cellulose, hydroxypropylmethyl cellulose)), gelatins including non-gelling and gelling types (e.g., mammalian gelatins such as bovine gelatin, porcine gelatins, avian gelatins, fish gelatins (e.g., mixed high molecular weight and low molecular weight gelatins), synthetic polymers (e.g., polyvinylpyrrolidones, polyethylene oxide and/or polypropylene oxide polymers and copolymers (e.g., poloxamers, such as poloxamer 188), polyacrylate polymers (e.g., carbopols), polyamide polymers), sugars and sugar alcohols (e.g., dextrose, lactose, galactose, glucose, ribose, sucrose, trehalose, mannitol, maltitol, lactitol, sorbitol, xylitol, erythritol, galactitol, inositol) polypeptides/proteins, amino acids, inorganic or organic acids (e.g., citric acid, lactic acid, malic acid, gluconic acid, benzoic acid, toluenesulfonic acid, phosphoric acid, sulfuric acid, hydrochloric acid, tartaric acid, oxalic acid, cyclamic acid, ascorbic acid, methanesulfonic acid, benzenesulfonic acid, formic acid) and their salts (e.g., sodium, potassium, calcium, magnesium, lithium, ammonium salts of aforementioned acids), inorganic or organic bases (e.g., alkali metal or alkaline earth metal carbonates, bicarbonates, hydroxide, oxides), anionic surfactants (e.g., sodium lauryl sulfate, sodium laureth sulfate, sodium dodecylbenzenesulfonate, sodium lauroyl sarcosinate, sodium stearate), cationic surfactants (e.g., benzalkonium halides, cetylpyridinium halides, cetrimonium halides, benzethonium halides), zwitterionic surfactants (e.g., cocamidoalkyl betaines, such as cocamidopropyl betaine), nonionic surfactants (e.g., fatty alcohol ethoxylates (e.g., polyethylene glycol polydodecyl ethers), sorbitan esters (e.g., sorbitan monolaurate, sorbitan monooleate, sorbitan monopalmitate, sorbitan monostearate, sorbitan tristearate), polyethoxylated sorbitan esters (e.g., polysorbate 20, polysorbate 40, polysorbate 60, polysorbate 80), and antioxidants (e.g., ascorbic acid, sodium metabisulfite, BHT, BHA, TBHQ, propyl gallate, beta-carotene, tocopherols, tocotrienols).

5.12. Formula 5.11, wherein any one or more of said excipients are present in an amount of 0.01 to 20% by weight of the formulation, e.g., 0.01 to 15%, or 0.01 to 10%, or 0.1 to 20%, or 0.1 to 15% or 0.1 to 10%, or 0.5 to 10%, or 0.5 to 5%, or 1 to 5%, or 2.5 to 5%, or 1 to 3%, or 0.1 to 1%.

5.13. Any preceding formulation which is free of added plasticizer, surfactant or humectant (e.g., polyol).

5.14. Any preceding formulation, wherein the formulation comprises from 0.01 to 99% water, for example, from 0.01 to 10% water, or from 0.01 to 5% water, or from 50 to 99% water, or from 75 to 99% water, or from 25 to 75% water.

5.15. Any preceding formulation, wherein the formulation is a rapidly dissolving tablet or wafer, e.g., a sublingual tablet or wafer.
5.16. Any of formulations 5 or 5.1 to 5.14, wherein the formulation is an oral spray, e.g., a sublingual spray or buccal spray.
5.17. Any of formulations 5 or 5.1 to 5.14, wherein the formulation is a rapidly dissolving film, e.g., a sublingual film or buccal film.
5.18. Formulation 5.17, wherein the film is a single layer or multi-layer film.
5.19. Formulation 5.17 or 5.18, wherein the film has uniform or substantially uniform thickness.
5.20. Formulation 5.17, 5.18 or 5.19 wherein the Compound of Formula III is uniformly or substantially uniformly distributed throughout the film.
5.21. Any of formulations 5 or 5.1 to 5.14, wherein the formulation is an intranasal spray.
5.22. Any of formulations 5 or 5.1 to 5.14, wherein the formulation is an oral gel, e.g., a rapidly dissolving sublingual or buccal gel.
5.23. Any of formulations 5 or 5.1 to 5.14, wherein the formulation is an intravaginal formulation, e.g., an intravaginal rapidly dissolving tablet, wafer or gel, or an intravaginal spray or an intravaginal rapidly dissolving film.
5.24. Any preceding formulation wherein the Compound of Formula III is incorporated into the formulation as microparticles (e.g., particles having an average diameter of less than 50 μm, less than 30 μm, less than 10 μm, or less than 5 μm, or less than 1 μm).
5.25. Any preceding formulation wherein the Compound of Formula III is incorporated into the formulation as nanoparticles (e.g., particles having an average diameter of less than 100 nm, or less than 50 nm, or less than 10 nm).
5.26. Any preceding formulation, wherein the formulation is absorbed by the mucosa (e.g., dissolves) in less than 30 seconds after administration.
5.27. Any preceding formulation, wherein the dosage of the Compound of Formula III is from 1 to 20% of the unit daily dosage for oral administration, for example, 5 to 15% of the oral dosage.
5.28. Any preceding formulation, wherein the formulation further comprises the Compound of Formula II or the Compound of Formula I or a combination thereof.
5.29. Any preceding formulation, wherein the formulation is formulated for administration once per day, or twice per day, or three times per day, or four times per day, or once every two days, or once every three days.
5.30. Any preceding formulation, wherein the formulation comprises the Compound of Formula III in tosylate salt form, e.g., in mono-tosylate salt form or di-tosylate salt form, or a mixture thereof.
5.31. Formulation 5.30, wherein the formulation further comprises toluenesulfonic acid, e.g., wherein the formulation comprises the Compound of Formula III in tosylate salt form and toluenesulfonic acid in a ratio of 1:3 to 3:1, or 1:2 to 2:1 or 1:1.5 to 1.5:1, or about 1:1.

In a sixth embodiment, the present disclosure provides a subcutaneous pharmaceutical formulation (Formulation 6) comprising 1-(4-fluoro-phenyl)-4-((6bR,10aS)-1,1,2,2-d$_4$-3-methyl-2,3,6b,9,10,10a-hexahydro-1H,7H-pyrido[3',4':4,5]pyrrolo[1,2,3-de]quinoxalin-8-yl)-butan-1-one (Compound of Formula III), in free base, co-crystal or salt form. The present disclosure further provides the following Formulations:

6.1. Formulation 6, wherein the formulation comprises the Compound of Formula III in free base form.
6.2. Formulation 6, wherein the formulation comprises the Compound of Formula III in salt form, e.g., in pharmaceutically acceptable salt form, optionally in amorphous solid or crystal salt form; or in co-crystal form, e.g., in nicotinamide or isonicotinamide co-crystal form.
6.3. Formulation 6.2, wherein the salt form is a tosylate, oxalate, cyclamate, 4-aminosalicylate, or hydrochloride salt form, optionally, wherein said salt form is a crystal salt form.
6.4. Any preceding formulation, wherein the formulation comprises from 0.01 to 100 mg of the Compound of Formula III (free base equivalent), e.g., 0.01 to 75 mg, 0.01 to 50 mg, 0.01 to 30 mg, 0.01 to 20 mg, 0.1 to 20 mg, 5 to 20 mg, 10 to 20 mg, 10 to 30 mg, 20 to 30 mg, 20 to 50 mg, or 50 to 100 mg.
6.5. Any preceding formulation, wherein the formulation comprises from 0.01 to 10 mg of the Compound of Formula III (free base equivalent).
6.6. Any preceding formulation, wherein the formulation comprises from 0.05 to 8 mg of the Compound of Formula III (free base equivalent), e.g., from 0.1 to 5 mg, or from to 5 to 10 mg.
6.7. Any preceding formulation, further comprising one or more of water, water soluble-polymers (e.g., modified celluloses, polyvinylpyrrolidones, polyethylene glycols), water-miscible alcohols (e.g., ethanol, glycerin and propylene glycol), bulking agents (e.g., sugars, sugar alcohols, and amino acids), inorganic salts (e.g. sodium chloride, calcium chloride, potassium chloride), buffers (e.g., carbonate and bicarbonate salts, citrate salts, phosphate salts, Tris salts), preservatives, antioxidants, chelating agents, and mixtures thereof.
6.8. Any preceding formulation, wherein the formulation comprises from 0.01 to 99% water, for example, from 0.01 to 10% water, or from 0.01 to 5% water, or from 50 to 99% water, or from 75 to 99% water, or from 25 to 75% water.
6.9. Any preceding formulation, wherein a substantial amount (e.g., greater than 75% or greater than 85%, or greater than 90%) of the Compound of Formula III is absorbed immediately (e.g., in less than 1 minute, or less than 5 minutes).
6.10. Any preceding formulation, wherein a significant amount (e.g., greater than 25%, or greater than 50% or greater than 75%) of the Compound of Formula III is not absorbed immediately (e.g., in greater than 5 minutes, or greater than 10 minutes, or greater than 30 minutes, or greater than 1 hour, or greater than 5 hours).
6.11. Any preceding formulation, wherein the formulation is packaged for use in a pre-filled syringe, a pre-filled auto-injector, or a sealed vial or similar container.
6.12. Any preceding formulation, wherein the formulation is packaged for use as a dry solid, e.g., a lyophilized solid, for reconstitution in a pharmaceutically acceptable solvent (e.g., sterile water for injection) at the point of use.
6.13. Any preceding formulation, wherein the dosage of the Compound of Formula III is from 1 to 20% of the unit daily dosage for oral administration, for example, 5 to 15% of the oral dosage.
6.14. Any preceding formulation, wherein the formulation further comprises the Compound of Formula II or the Compound of Formula I, or a combination thereof.

6.15. Any preceding formulation, wherein the formulation is formulated for administration once per day, or once every two days, or once every three days, or once per week, or once every two weeks, or once every three weeks, or once per month, or once every two months, or once every three months, or once every six months.

6.16. Any preceding formulation, wherein the formulation comprises the Compound of Formula III in tosylate salt form, e.g., in mono-tosylate salt form or di-tosylate salt form, or a mixture thereof.

6.17. Formulation 4.16, wherein the formulation further comprises toluenesulfonic acid, e.g., wherein the formulation comprises the Compound of Formula III in tosylate salt form and toluenesulfonic acid in a ratio of 1:3 to 3:1, or 1:2 to 2:1 or 1:1.5 to 1.5:1, or about 1:1.

As used herein, "deuteration" refers to the substitution of a hydrogen (protium, $^1H$) atom in a chemical structure with a deuterium atom ($^2H$). A hydrogen atom position of a structure is considered substituted with deuterium when the abundance of deuterium at that position is enriched. The natural abundance of deuterium is about 0.02%, so a compound is "enriched" with deuterium at a specific position when the frequency of incorporation of deuterium at that position exceeds 0.02%. Therefore, in any embodiment of a deuterated compound provided herein, any one or more hydrogen atoms may be enriched with deuterium at a level of greater than 0.1%, or greater than 0.5%, or greater than 1%, or greater than 5%, such as, greater than 50%, or greater than 60%, or greater than 70%, or greater than 80%, or greater than 90% or greater than 95%, or greater than 96%, or greater than 97%, or greater than 98%, or greater than 99%.

In all aspects and embodiments of the present disclosure comprising the Compound of Formula I, said Compound of Formula I may optionally be deuterated at one or more hydrogen atom positions.

In all aspects and embodiments of the present disclosure comprising the Compound of Formula II, said Compound of Formula II is enriched only at the designated positions $(2,2-d_2)$.

In all aspects and embodiments of the present disclosure comprising the Compound of Formula III, said Compound of Formula III is enriched only at the designated positions $(1,1,2,2-d_4)$.

In a second aspect, the present disclosure provides a process (Process 1) for the production of the transmucosal formulation of Formulation 1, et seq., or Formulation 2, et seq., or Formulation 5, et seq., comprising the steps of:
(a) combining the Compound of Formula I, in free or pharmaceutically acceptable salt form, and/or the Compound of Formula II, in free or pharmaceutically acceptable salt form, and/or the Compound of Formula III, in free or pharmaceutically acceptable salt form, with suitable pharmaceutically acceptable excipients, optionally in a suitable solvent or mixture of solvents; and
(b) either (1) removing the solvent to provide a dried film, or (2) removing the solvent to provide a dried powder suitable for compression into tablets or wafers, or (3) remove the solvent, or some portion thereof, to provide a solution suitable for administration via an aerosol spray device.

In a third aspect, the present disclosure provides a process (Process 2) for the production of the subcutaneous formulation of Formulation 3, et seq., or Formulation 4, et seq., or Formulation 6, et seq., comprising the steps of either:

(a) Combining the Compound of Formula I, in free or pharmaceutically acceptable salt form, and/or the Compound of Formula II, in free or pharmaceutically acceptable salt form, and/or the Compound of Formula III, in free or pharmaceutically acceptable salt form, with suitable pharmaceutically acceptable excipients in a suitable solvent or mixture of solvents for injection, and then packaging the resulting solution for use (e.g., in a pre-filled syringe, or in a sealed vial or similar container, or in a pre-filled auto-injector); or
(b) Combining the Compound of Formula I, in free or pharmaceutically acceptable salt form, and/or the Compound of Formula II, in free or pharmaceutically acceptable salt form, and/or the Compound of Formula III, in free or pharmaceutically acceptable salt form, optionally with suitable pharmaceutically acceptable excipients, in a suitable solvent or mixture of solvents, and then removing said solvent(s) to obtain a dry solid (e.g., a lyophilized solid) for packaging.

The pharmaceutical formulations disclosed herein, e.g., Formulation 1, et seq., Formulation 2, et seq., Formulation 3, et seq., Formulation 4, et seq., Formulation 5, et seq., and Formulation 6, et seq., may comprise any suitable pharmaceutically acceptable excipients, including but not limited to: diluents such as starches, pregelatinized starches, lactose, powdered celluloses, microcrystalline celluloses, dicalcium phosphate, tricalcium phosphate, mannitol, sorbitol, xylitol, sugar and the like; binders such as acacia, guar gum, gum tragacanth, gelatin, polyvinylpyrrolidones such as polyvinylpyrrolidones (PVP K-30,K-90), poly (vinyl pyrrolidone-co-vinyl acetate) (PVP-VA) and the like, hydroxypropyl celluloses, hydroxypropyl methylcellulose, cellulose acetate, hydroxypropyl methylcellulose acetate succinate (HPMC-AS) and the like; disintegrants such as starches, sodium starch glycolate, pregelatinized starches, crospovidones, croscarmellose sodium and the like; lubricants such as stearic acid, magnesium stearate, zinc stearate and the like; glidants such as colloidal silicon dioxide and the like; solubility or wetting enhancers such as anionic or cationic or neutral surfactants; maltodextrin, complex forming agents such as various grades of cyclodextrins and resins; release rate controlling agents such as hydroxypropyl celluloses, hydroxymethyl celluloses, hydroxypropyl methylcelluloses, ethylcelluloses, methylcelluloses, various grades of methyl methacrylates, waxes and the like; and film formers, plasticizers, colorants, flavoring agents, sweeteners, viscosity enhancers, preservatives, antioxidants, buffering agents, bulking agents, and the like.

In some embodiments, the formulations may further comprise one or more anti-oxidants, for example, tocopherol, butylated hydroxytoluene (BHT), propyl gallate (OPG), or and ascorbic acid, or the like. The inclusion of an anti-oxidant may further improve the chemical stability of the formulations by preventing oxidative chemical degradation of the active ingredient.

In another aspect, the present disclosure provides Formulation 1, et seq., Formulation 2, et seq., Formulation 3, et seq., Formulation 4, et seq., Formulation 5, et seq., or Formulation 6, et seq., for use in treating a disease or abnormal condition involving or mediated by the 5-HT$_{2A}$ receptor, serotonin transporter (SERT), and/or dopamine D$_1$/D$_2$ receptor signaling pathways, e.g., a disorder selected from obesity, anorexia, bulimia, depression (including major depressive disorder (MDD)), anxiety, psychosis, schizophrenia, obsessive-compulsive disorder, sexual disorders, migraine, attention deficit disorder, attention deficit hyperactivity disorder, sleep disorders, conditions associated with cephalic pain, social phobias, dementia (including Alzheimer's Disease and Parkinson's dementia), gastrointestinal disorders such as dysfunction of gastrointestinal tract motility and obesity, or bipolar disorder (e.g., bipolar depression).

In another embodiment, the invention provides a method (Method 1) for the prophylaxis or treatment of a disease or abnormal condition involving or mediated by the 5-HT$_{2A}$ receptor, serotonin transporter (SERT), and/or dopamine D$_1$/D$_2$ receptor signaling pathways, in a patient in need thereof, comprising administering to the patient by a transmucosal or subcutaneous route, a therapeutically effective amount of the Compound of Formula I and/or the Compound of Formula II and/or the Compound of Formula III. Further embodiments of Method 1 include:

1.1 Method 1, wherein the Compound of Formula I and/or the Compound of Formula II and/or the Compound of Formula III is administered via a transmucosal route (e.g., intra-orally, intra-nasally, by buccal absorption or by sublingual absorption).
1.2 Method 1.1, wherein the Compound of Formula I and/or the Compound of Formula II and/or the Compound of Formula III is administered in the form of a composition selected from any of Formulation 1, et seq., or Formulation 2, et seq. or Formulation 4, et seq.
1.3 Method 1.1 or 1.2 wherein the Compound of Formula I and/or the Compound of Formula II and/or the Compound of Formula III is administered sublingually, e.g., via a sublingual film, sublingual spray, sublingual tablet or wafer (e.g., fast-dissolving tablet or wafer), or a sublingual solution (e.g., aqueous solution).
1.4 Method 1.1 or 1.2 wherein the Compound of Formula I and/or the Compound of Formula II and/or the Compound of Formula III is administered buccally, e.g., via a buccal film, buccal spray, buccal sublingual tablet or wafer (e.g., fast-dissolving tablet or wafer).
1.5 Method 1.1 or 1.2 wherein the Compound of Formula I and/or the Compound of Formula II and/or the Compound of Formula III is administered intraorally, e.g., via an intra-oral spray (e.g., an aerosol spray).
1.6 Method 1.1 or 1.2 wherein the Compound of Formula I and/or the Compound of Formula II and/or the Compound of Formula III is administered intranasally, e.g., via an intranasal spray (e.g., an aerosol spray).
1.7 Method 1, wherein the Compound of Formula I and/or the Compound of Formula II and/or the Compound of Formula III is administered via a subcutaneous route (e.g., a subcutaneous injection).
1.8 Method 1.7, wherein the Compound of Formula I and/or the Compound of Formula II and/or the Compound of Formula III is administered in the form of a composition selected from any of Formulation 3, et seq., or Formulation 4, et seq. or Formulation 6, et seq.
1.9 Method 1.7 or 1.8 wherein the Compound of Formula I and/or the Compound of Formula II and/or the Compound of Formula III is administered via a pre-filled syringe, an auto-injector, a wearable injector.
1.10 Method 1.7, 1.8 or 1.9 wherein the Compound of Formula I and/or the Compound of Formula II and/or the Compound of Formula III is administered by the patient (e.g., is self-administered).
1.11 Method 1 or any of 1.1, et seq., wherein the disease or condition is selected from obesity, anorexia, bulimia, depression (including major depressive disorder (MDD)), anxiety, psychosis, schizophrenia, obsessive-compulsive disorder, sexual disorders, migraine, attention deficit disorder, attention deficit hyperactivity disorder, sleep disorders, conditions associated with cephalic pain, social phobias, dementia (including Alzheimer's Disease and Parkinson's dementia), gastrointestinal disorders such as dysfunction of gastrointestinal tract motility and obesity, or bipolar disorder (e.g., bipolar depression).
1.12 Method 1 or any of 1.1, et seq., wherein the disease or condition to be treated requires rapid intervention, e.g., acute anxiety, acute agitation, or acute psychosis.
1.13 Method 1 or any of 1.1, et seq., wherein the dosage administered via the transmucosal (e.g., sublingual, buccal, intranasal or intraoral route) or subcutaneous route is from 1 to 20% of the dosage administered for the same condition by the oral route, for example, 5 to 15% of the oral dosage.

A Compound of Formula I or a Compound of Formula II and/or a Compound of Formula III, for use in Method 1 or any of Method 1.1 et seq.

A pharmaceutical composition selected from any of Formulation 1, et seq., Formulation 2, et seq., Formulation 3, et seq., Formulation 4, et seq., Formulation 5, et seq., or Formulation 6, et seq., for use in Method 1 or any of Method 1.1 et seq.

Use of a Compound of Formula I or a Compound of Formula II or a Compound of Formula III in the manufacture of a medicament for transmucosal or subcutaneous administration, e.g., a medicament in accordance with any of Formulation 1, et seq., Formulation 2, et seq., Formulation 3, et seq., Formulation 4, et seq., Formulation 5, et seq., or Formulation 6, et seq., for use in a method of treatment according to Method 1 or any of Method 1.1 et seq.

Methods of synthesizing the Compounds of Formula I and the Compounds of Formula II are known in art, and include the methods disclosed in WO PCT/US08/03340 (WO 2008/112280); U.S. application Ser. No. 10/786,935; U.S. Pat. Nos. 6,548,493; 7,238,690; 6,552,017; 6,713,471; 7,183,282; U.S. RE39680, and U.S. RE39679, and WO 2015/154025, the contents of each of which are incorporated by reference in their entirety. Salts of the Compounds of the Invention may also be prepared as similarly described in U.S. Pat. Nos. 6,548,493; 7,238,690; 6,552,017; 6,713,471; 7,183,282; U.S. RE39680; U.S. RE39679; and WO 2009/114181, the contents of each of which are incorporated by reference in their entirety.

Isolation or purification of the diastereomers of the Compounds of the Invention may be achieved by conventional methods known in the art, e.g., column purification, preparative thin layer chromatography, preparative HPLC, crystallization, trituration, simulated moving beds and the like.

The pharmaceutically acceptable salts of the Compounds of Formula I, II and III can be synthesized from the parent compound which contains a basic or acidic moiety by conventional chemical methods. Generally, such salts can be prepared by reacting the free base forms of these compounds with a stoichiometric amount of the appropriate acid in water or in an organic solvent, or in a mixture of the two; generally, non-aqueous media like ether, ethyl acetate, ethanol, isopropanol, or acetonitrile are preferred. Further details for the preparation of these salts, e.g., toluenesulfonic salt in amorphous or crystal form, may be found in PCT/US08/03340 and/or U.S. Provisional Appl. No. 61/036,069.

Transmucosal dosage forms are known to those skilled in the art, and general procedures by which these dosage forms can be prepared have been described. Examples of dissolvable film delivery systems include those disclosed in U.S. Pat. No. 4,136,145 to Fuchs, U.S. Pat. No. 4,849,246 to Schmidt, U.S. Pat. No. 5,629,003 to Horstmann, U.S. Pat.

No. 5,948,430 to Zerbe, U.S. Pat. No. 9,108,340 to Yang, U.S. Pat. No. 8,906,277 to Yang, U.S. Pat. No. 8,900,498 to Yang, U.S. Pat. No. 8,900,497 to Yang, U.S. Pat. No. 8,652,378 to Yang, U.S. Pat. No. 8,603,514 to Yang, U.S. Pat. No. 9,427,412 to Bryson, and U.S. Pat. No. 8,414,922 to Bryson. The preparation of other transmucosal systems are disclosed in U.S. Pat. No. 5,763,476 to Delbressine (sublingual and buccal solutions and solids), U.S. Pat. No. 9,216,175 to Amancha (sublingual spray), U.S. Pat. No. 8,835,459 to Kottayil (sublingual spray), and U.S. Pat. No. 6,552,024 to Chen (various mucosal delivery systems). The contents of each of these references is incorporated by reference herein in their entireties.

EXAMPLES

Example 1A: Comparison of Pharmacokinetics Between Subcutaneous (SC) and Sublingual (SL) Dosing in Dogs In vivo absorption and distribution of the Compound of Formula I and the Compound of Formula II, both in their tosylate salt forms, is compared between subcutaneous and sublingual administration in non-cross over sequential studies in dogs.

SC Administration: Six male beagle dogs between 2 and 5 years of age are randomized in two groups of three dogs each. Dogs in group 1 are administered the Compound of Formula I at a dose of 1 mg/kg (free base equivalent) in a 0.5% methylcellulose/distilled water vehicle. Dogs in group 2 are administered the Compound of Formula II at a dose of 1 mg/kg (free base equivalent) in a 0.5% methylcellulose/distilled water vehicle. Administration is subcutaneous in the intrascapular region via a 22 or 23 gauge needle. Whole blood samples are collected via the dog's cephalic vein pre-dose, and at post-dose time-points 5, 15 and 30 minutes, 1, 2, 4, 6, 8 and 24 hours. Following a minimum 7-day washout period, the dogs are transferred to the sublingual portion of the study.

SL Administration: The dogs of group 1 are administered the Compound of Formula I at a dose of 1 mg/kg (free base equivalent) in a 0.5% methylcellulose/distilled water vehicle. Dogs in group 2 are administered the Compound of Formula II at a dose of 1 mg/kg (free base equivalent) in a 0.5% methylcellulose/distilled water vehicle. The animals are anesthetized prior to administration of the dose using propofol (6 mg/kg) and anesthesia is maintained for 30 minutes using 3-4.5% isoflurane. Administration is sublingual and the dosage is applied for 30 minutes, then wiped off using unwoven gauze. Whole blood samples are collected via the dog's cephalic vein pre-dose, and at post-dose time-points 5, 15 and 30 minutes, 1, 2, 4, 6, 8, 24, 36 and 48 hours.

All blood samples are processed to plasma and analyzed for drug concentrations using liquid chromatography-tandem mass spectrometry (LC-MS/MS). Area under the curve (AUC) of parent and metabolites based on plasma versus time data are calculated using Prism 5.04 software (GraphPad Software, Inc.).

The results are summarized in Table 1A below (AUC is shown for 0-24 hours):

|  | Test Compound (1 mg/kg): | Formula I | Formula II |
|---|---|---|---|
| SL | AUC (ng-hr/mL) | 734 | 1262 |
|  | Cmax (ng/mL) | 259 | 562 |
|  | Tmax (hr) | 1.0 | 1.0 |
| SC | AUC (ng-hr/mL) | 813 | 785 |
|  | Cmax (ng/mL) | 110 | 79 |
|  | Tmax (hr) | 1.0 | 1.0 |

The results demonstrate that both SC and SL dosing results in high plasma concentration and high plasma AUC. SL dosing also results in significantly higher maximal plasma concentration of drug (Cmax) compared to SC dosing for both compounds. For the Compound of Formula II, SL dosing also results in a significantly higher overall AUC, while the AUC for the Compound of Formula I shows comparable AUC between SC and SL dosing. Time to maximum plasma concentration is also the same between SC and SL dosing for both compounds.

Example 1B: Comparison of Pharmacokinetics Between Subcutaneous and Sublingual Dosing in Dogs with Metabolite Analysis A second study is performed substantially as described for Example 1A, except that plasma samples are analyzed for the parent (administered) compounds, as well as for the major known metabolites. After administration of either the Compound of Formula I or the Compound of Formula II, the major circulating species are found to be the parent and the N-desmethyl metabolite. The results are summarized in Table 1B below (AUC is shown for 0-24 hours):

|  | Test Compound (1 mg/kg): | Formula I | Formula II |
|---|---|---|---|
| SL | AUC (ng-hr/mL)-Parent | 507 | 1262 |
|  | Cmax (ng/mL)-Parent | 179 | 562 |
|  | Tmax (hr)-Parent | 1.0 | 1.0 |
|  | AUC (ng-hr/mL)-Des-methyl | 23 | 104 |
|  | Cmax (ng/mL)-Des-methyl | 4.0 | 27 |
|  | Tmax (hr)-Des-methyl | 1.0 | 1.0 |
| SC | AUC (ng-hr/mL)-Parent | 560 | 785 |
|  | Cmax (ng/mL)-Parent | 76 | 79 |
|  | Tmax (hr)-Parent | 1.0 | 1.0 |
|  | AUC (ng-hr/mL)-Des-methyl | 20 | 49 |
|  | Cmax (ng/mL)-Des-methyl | 4.0 | 1.0 |
|  | Tmax (hr)-Des-methyl | 1.7 | 1.0 |

These results further demonstrate that both SC and SL dosing results in high plasma concentration and high plasma AUC for the administered compounds. SL dosing also results in higher maximal plasma concentration of drug (Cmax) compared to SC dosing for both compounds. In addition, the results show that both SC and SL dosing results in very low rates of metabolite formation, indicating that these routes effectively bypass the primary site of metabolic degradation of these compounds (hepatic metabolism). The Compound of Formula I circulated in plasma at an AUC approximately 22 times higher for parent than metabolite after SL dosing, and 27 times higher for SC dosing. In contrast, when administered orally, it has been found that the Compound of Formula I and its desmethyl metabolite circulate in plasma with AUC's of about 1:1 or less. Similarly, results are shown for the Compound of Formula II (parent/metabolite ratio of about 12 for SL and about 16 for SC).

Example 2: Pharmacokinetics of Oral Dosing in Dogs

In contrast to the subcutaneous and sublingual pharmacokinetics presented in Example 1, this Example demonstrates that oral administration results in substantially lower systemic exposure to drug, due to the high extent of hepatic first-pass metabolism. This is true even using doses from 2.5 times to 15 times higher than the dose used in the SC and SL study.

As part of a larger long-term toxicology study, 20 male and female beagle dogs are administered either control, or the Compound of Formula I, tosylate salt form, at a dose of 2.5, 5, 10, or 15 mg/kg. For control, the dogs are administered empty capsules. For the Compound of Formula I, the dogs are administered normal-release oral capsules. Blood samples are obtained at 0.25 hours, 0.5 hours, 1 hour, 4 hours, 8 hour and 24 hours. The blood samples are processed to plasma and analyzed for concentration of the Compound of Formula I by high-performance liquid chromatography-mass spectrometry. Cmax, Tmax and area-under-the-curve (AUC, 0-24 hours) are calculated using Phoenix WinNonlin software. The results are shown in Table 1 below:

| Dosing: | 2.5 mg/kg | 5 mg/kg | 10 mg/kg | 15 mg/kg |
|---|---|---|---|---|
| AUC (ng-hr/mL) | 40.05 | 52.45 | 142.5 | 248 |
| Cmax (ng/mL) | 5.51 | 7.72 | 29.0 | 44.5 |
| Tmax (hr) | 0.469 | 0.875 | 0.813 | 1.63 |

The Compound of Formula I shows dose-dependent oral absorption, and that the plasma concentration achieved with even the highest-oral dose is far below the plasma concentration and AUC achieved from sublingual and subcutaneous administration as shown in Example 1. Sublingual and subcutaneous dosing of the Compound of Formula I at only 1.0 mg/kg results in 24-hour AUC that is more than 18× higher than oral dosing at 2.5 mg/kg. Sublingual and subcutaneous doing even provide 24-hour AUC about three times higher at 1.0 mg/kg than oral dosing at 15 mg/kg.

These results taken together clearly demonstrate the large loss in exposure resulting from hepatic first pass metabolism, and the unexpectedly high improvement in exposures that are achieved from using transmucosal dosing systems.

Example 3: Pharmacokinetics of SC and IV Dosing in Monkeys

A study is also performed in monkeys to determine the plasma concentrations of both the Compound of Formula I and its major metabolites after both SL and SC dosing at 0.5 mg/kg. Six Cynomolgus monkeys are divided into two groups for IV and SC dosing with the Compound of Formula I. The animals are dosed in a fasting state. Blood samples are collected pre-dose, and at 5 minutes, 15 minutes, 1, 2, 4, 6, 8, 24, 36 and 48 hours post-dose. All blood samples are processed to plasma and later analyzed by liquid chromatography-tandem mass spectrometry. Samples are tested for the concentration of the Compound of Formula I, as well as for its five major known metabolites. PK parameters are calculated using PK Solutions 2.0 software (Summit Research Services, Colorado, US).

The results show that bioavailability (based on a comparison of IV to SC pharmacokinetics) is about 74% for the Compound of Formula I or SC administration. Most tested metabolites are found to present at levels below the limit of quantitation. Only the des-methyl metabolite and the amide metabolite (oxidation of the methylene adjacent to the N-methyl group to a carbonyl) are found to be present in significant concentration. The concentrations of both metabolites are found to be lower after SC dosing than after IV dosing. The results are shown in Table 3 below:

| | Analyte: | Parent Compound | Des-methyl metabolite | Amide Metabolite |
|---|---|---|---|---|
| IV | AUC (ng-hr/mL) | 297 | 9.2 | 20 |
| | Cmax (ng/mL) | 94 | 1.5 | 1.9 |
| | Tmax (hr) | 0.083 | 1.0 | 4.0 |
| SC | AUC (ng-hr/mL) | 220 | 2.3 | 3.3 |
| | Cmax (ng/mL) | 23 | 0.3 | 0.3 |
| | Tmax (hr) | 2.0 | 2.0 | 6.0 |

The results show that SC administration in monkeys results in substantially lower levels of formation of the major metabolites compared to IV administration.

What is claimed:

1. A transmucosal pharmaceutical formulation comprising 1-(4-fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one (Compound of Formula I) in free base, co-crystal or salt form, or comprising 1-(4-fluoro-phenyl)-4-(6bR,10aS)-2,2-$d_2$-3-methyl-2,3,6b,9,10,10a-hexahydro-1H,7H-pyrido[3',4':4,5]pyrrolo[1,2,3-de]quinoxalin-8-yl)-butan-1-one (Compound of Formula II) in free base, co-crystal or salt form, or comprising -(4-fluoro-phenyl)-4-((6bR,10aS)-1,1,2,2-$d_4$-3-methyl-2,3,6b,9,10,10a-hexahydro-1H,7H-pyrido[3',4':4,5]pyrrolo[1,2,3-de]quinoxalin-8-yl)-butan-1-one (Compound of Formula III) in free base, co-crystal or salt form;
   wherein the formulation is a rapidly dissolving tablet or wafer, a sublingual tablet or wafer, a rapidly dissolving film, sublingual film, buccal film, oral gel, or a rapidly dissolving sublingual or buccal gel.

2. The formulation of claim 1, wherein the formulation comprises the Compound of Formula I or the Compound of Formula II or the Compound of Formula III in free base form.

3. The formulation of claim 1, wherein the formulation comprises the Compound of Formula I or the Compound of Formula II or the Compound of Formula III in salt form.

4. The formulation of claim 3, wherein the salt form is tosylate.

5. The formulation of claim 1, wherein the formulation comprises from 0.01 to 10 mg of the Compound of Formula I (free base equivalent) or the Compound of Formula II (free base equivalent) or the Compound of Formula III (free base equivalent).

6. The formulation of claim 1, further comprising one or more hydrophilic water-soluble or water swellable polymers.

7. The formulation of claim 6, wherein the polymer is selected from the group consisting of natural or modified cellulosic polymers, polymers of ethylene oxide and/or propylene oxide, polymers comprising acrylic acid monomers, natural or modified gums, natural or modified starches, or any mixture thereof.

8. The formulation of claim 1, further comprising one or more excipients selected from the group consisting of plasticizers, surfactants, drying agents, flavors, sweeteners, binders, disintegrants, humectants, wetting agents, antioxidants, buffering agents, and thickening agents.

9. The formulation of claim 1, wherein the formulation is a rapidly dissolving tablet or wafer, or a sublingual tablet or wafer.

10. The formulation of claim 1, wherein the formulation is an oral spray, or a sublingual spray or buccal spray.

11. The formulation of claim 1, wherein the formulation is a rapidly dissolving film or a sublingual film or buccal film.

12. The formulation of claim 11, wherein the film has uniform or substantially uniform thickness.

13. The formulation of claim 11, wherein the Compound of Formula I or II or III is uniformly or substantially uniformly distributed throughout the film.

14. The formulation of claim 1, wherein the formulation is an intranasal spray.

15. The formulation of claim 1, wherein the formulation is an oral gel or a rapidly dissolving sublingual or buccal gel.

16. The formulation of claim 1, wherein the formulation is an intravaginal formulation, or an intravaginal rapidly dissolving tablet, wafer or gel, or an intravaginal spray or an intravaginal rapidly dissolving film.

17. The formulation of claim 1, wherein the Compound of Formula I or the Compound of Formula II or the Compound of Formula III is incorporated into the formulation as microparticles.

18. The formulation of claim 1, wherein the Compound of Formula I or the Compound of Formula II or the Compound of Formula III is incorporated into the formulation as nanoparticles.

19. The formulation of claim 1, wherein the formulation is absorbed by the mucosa or dissolves in less than 30 seconds after administration.

20. A subcutaneous pharmaceutical formulation comprising 1-(4-fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one (Compound of Formula I) in free base, co-crystal or salt form, or comprising 1-(4-fluoro-phenyl)-4-((6bR,10aS)-2,2-$d_2$-3-methyl-2,3,6b,9,10,10a-hexahydro-1H,7H-pyrido[3',4':4,5]pyrrolo[1,2,3-de]quinoxalin-8-yl)-butan-1-one (Compound of Formula II) in free base, co-crystal or salt form, or comprising 1-(4-fluoro-phenyl)-4-((6bR,10aS)-1,1,2,2-$d_4$-3-methyl-2,3,6b,9,10,10a-hexahydro-1H,7H-pyrido[3',4':4,5]pyrrolo[1,2,3-de]quinoxalin-8-yl)-butan-1-one (Compound of Formula III) in free base, co-crystal or salt form.

21. The formulation of claim 1, wherein the formulation comprises the Compound of Formula I in tosylate salt form.

22. The formulation of claim 9, wherein the formulation comprises the Compound of Formula I in tosylate salt form.

23. The formulation of claim 11, wherein the formulation comprises the Compound of Formula I in tosylate salt form.

24. The formulation of claim 20, wherein the formulation comprises the Compound of Formula I in tosylate salt form.

* * * * *

UNITED STATES PATENT AND TRADEMARK OFFICE
CERTIFICATE OF CORRECTION

PATENT NO. : 10,716,786 B2
APPLICATION NO. : 15/934860
DATED : July 21, 2020
INVENTOR(S) : Peng Li et al.

Page 1 of 1

It is certified that error appears in the above-identified patent and that said Letters Patent is hereby corrected as shown below:

In the Claims

Claim 1, Column 24, Line 22-25, "1-(4-fluoro-phenyl)-4-(6bR,10aS)-2,2-$d_2$-3-methyl-2,3,6b,9,10,10a-hexahydro-1H,7H-pyrido[3',4':4,5]pyrrolo[1,2,3-de]quinoxaline-8-yl)-butan-1-one" should be changed to -- 1-(4-fluoro-phenyl)-4-((6bR,10aS)-2,2-$d_2$-3-methyl-2,3,6b,9,10,10a-hexahydro-1H,7H-pyrido[3',4':4,5]pyrrolo[1,2,3-de]quinoxaline-8-yl)-butan-1-one --

Claim 1, Column 24, Line 26-29, "-(4-fluoro-phenyl)-4-((6bR,10aS)-2,2-$d_2$-3-methyl-2,3,6b,9,10,10a-hexahydro-1H,7H-pyrido[3',4':4,5]pyrrolo[1,2,3-de]quinoxaline-8-yl)-butan-1-one" should be changed to -- 1-(4-fluoro-phenyl)-4-((6bR,10aS)-2,2-$d_2$-3-methyl-2,3,6b,9,10,10a-hexahydro-1H,7H-pyrido[3',4':4,5]pyrrolo[1,2,3-de]quinoxaline-8-yl)-butan-1-one --

Signed and Sealed this
Twenty-third Day of February, 2021

Drew Hirshfeld
*Performing the Functions and Duties of the
Under Secretary of Commerce for Intellectual Property and
Director of the United States Patent and Trademark Office*